(12) United States Patent
Bumcrot

(10) Patent No.: US 6,309,879 B1
(45) Date of Patent: Oct. 30, 2001

(54) HUMAN PATCHED GENES AND PROTEINS, AND USES RELATED THERETO

(75) Inventor: David H. Bumcrot, Belmont, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/207,857

(22) Filed: Dec. 8, 1998

Related U.S. Application Data

(60) Provisional application No. 60/067,940, filed on Dec. 8, 1997.

(51) Int. Cl.[7] ............................... C12N 5/16; C12N 1/21

(52) U.S. Cl. ................... 435/325; 435/320.1; 435/348; 435/349; 435/254.2; 435/252.3; 536/23.5; 530/350

(58) Field of Search .......................... 530/350; 536/23.5; 435/320.1, 252.3, 325, 348, 349, 254.2

(56) References Cited

U.S. PATENT DOCUMENTS 5,837,538    11/1998    Scott et al. ........................... 435/325

FOREIGN PATENT DOCUMENTS

| | | |
|---|---|---|
| 0 879 888 A2 | 11/1998 | (AT) . |
| 0 879 888 A2 | 11/1998 | (EP) . |
| 0879888AA | 11/1998 | (GB) . |
| WO 96/1120 | 4/1996 | (WO) . |
| WO 97/45541 | 12/1997 | (WO) . |
| WO9745541A1 | 12/1997 | (WO) . |
| WO 98/12326 | 3/1998 | (WO) . |
| WO 98/14475 | 4/1998 | (WO) . |
| WO 99/00117 | 1/1999 | (WO) . |
| WO 99/04775 | 2/1999 | (WO) . |

OTHER PUBLICATIONS

Fujiwara et al., Database EST, Accession No. D60319, HUM099A03B Clontech human fetal brain polyA+ mRNA (#6535) *Homo sapiens* cDNA clone GEN–099A03 5′, mRNA sequence, Aug. 1995.

Carpenter, D. et al., XP002101428, "Characterization of two patched receptors for the vertebrate hedgehog protein family", *Proc. Nat. Acad. Sci. USA*, vol. 95, No. 23, pp. 13630–13634 (1998).

Fujiwara, et al., XP002101429, "Human Fetal Brain cDNA 5′–end GEN–099A03 similar to none" (1995).

Takabatake, T. et al., XP002101427, "Hedgehog and patched gene expression in adult ocular tissues", *FEBS Letters*, vol. 410, pp. 485–489, (1997).

Carpenter, D. et al., "Characterization of two patched receptors for the vertebrate hedgehog protein family", Proc. Natl. Acad. Sci. USA, 95:13630–13634 (1998).

Fujiwara, T. et al. "Human Fetal brain cDNA 5′–end GEN–099A03 Similar to none", E.M.B.L. Databases, XP002101429 (1995).

Takabatake, T. et al., "Hedgehog and patched gene expression in adult ocular tissues", FEBS Letters, 410:485–489 (1997).

Carpenter, D. et al., "Characterization of two patched receptors for the vertebrate hedgehog protein family", *Proc. Natl. Acad. Sci. USA.*, 95(23): 13630–13634 (1998).

Chavrier, P. et al., "The complexity of the Rab and Rho GTP–binding protein subfamilies revealed by a PCR cloning approach", *Gene*, 112: 261–264 (1992).

Echelard, Y. et al., "Sonic hedgehog, a member of a family of putative signaling molecules, is implicated in the regulation of CNS polarity", *Cell*, 75: 1417–1430 (1993).

Forbes, A. et al., "Generic analysis of hedgehog signalling in the Drosophila embryo", *Development*, Supp.: 115–124 (1993).

Habuchi, T. et al., "Detailed deletion mapping of chromosome 9q in bladder cancer: evidence for two tumour suppressor loci", *Oncogene*, 11: 1671–1674 (1995).

Gorlin, R., "Nevoid basal–cell carcinoma syndrome", *Medicine*, 66: 98–113 (1987).

Hahn, H. et al., "A mammalian patched homolog is expressed in target tissues of sonic hedgehog and maps to a region associated with developmental abnormalities", *J. Biol. Chem.*, 271(21): 12125–12128 (1996).

Heemskerk, J. et al., "Drosophila hedgehog acts as a morphogen in cellular patterning", *Cell*, 76: 449–460 (1994).

Hidalgo, A. et al., "Cell pattering in Drosophila segment: spatial regulation of the segment polarity gene patched", *Development*, 110: 291–301 (1990).

Hooper, J. et al., "The Drosophila patched gene encodes a putative membrane protein required for segmental patterning", *Cell*, 59: 751–765 (1989).

Ingham, P., "Hedgehog points the way", *Curr. Biol.*, 4(4): 349–350 (1994).

(List continued on next page.)

*Primary Examiner*—Lorraine Spector
*Assistant Examiner*—Eileen B. O'Hara
(74) *Attorney, Agent, or Firm*—Ropes & Gray, LLP; Matthew P. Vincent; David P. Halstead

(57) ABSTRACT

The present invention relates to the discovery of a new member of the hedgehog receptor family, referred to herein as human ptc-2 (for patched-2 protein). The human ptc-2 polypeptides of the present invention include polypeptides which bind the products of the hedgehog gene family. Hedgehog family members are known for their broad involvement in the formation and maintenance of ordered spatial arrangements of differentiated tissues in vertebrates, both adult and embryonic, and can be used to generate and/or maintain an array of different vertebrate tissue both in vitro and in vivo.

13 Claims, No Drawings

OTHER PUBLICATIONS

Ingham, P. et al., "Role of the Drosophila patched gene in positional signalling", *Nature*, 353(6340): 184–187 (1991).

Krauss, S., et al., "A Functionally conserved homolog of the Drosophila segment polarity gene hh is expressed in tissues with polarizing activity in zebrafish embroys", *Cell*, 75: 1431–1444 (1993).

Ma. J. et al., "Molecular cloning and characterization of rK1k10, a cDNA encoding T–kininogenase fom rat submandibular gland and kidney", *Biochem.*, 31: 10922–10928 (1992).

Nakano, Y. et al., "A protein with several possible membrane–spanning domains encoded by the Drosophila segment polarity gene patched", *Nature*, 341: 508–513 (1989).

Phillips, R. et al., "The Drosophila segment polarity gene patched is involved in a position–signalling mechanism in imaginal discs", *Development*, 110: 105–114 (1990).

Quinn, A. et al., "Delineation to two distinct deleted regions on chromosome 9 in human non–melanoma skin cancers", *Genes Chromosome Cancer*, 11: 222–225 (1994).

Quinn, A. et al., "Chromosome 9 allele loss occurs in both basal and squamus cell carcinomas of the skin", *J. Invest. Dermatol.*, 102: 300–303 (1994).

Riddle, R. et al., "Sonic hedgehog mediates mediates the polarizing activity of the ZPA", *Cell*, 75: 1401–1416 (1993).

Roelink, H. et al., "Floor plate and motor neuron induction by vhh–1, a vertebrate homolog of hedgehog expressed by the notocord", *Cell*, 76: 761–775 (1994).

Sampedro, J. et al., "Unrestricted expression of the Drosophila gene patched allows a normal segment polarity", *Nature*, 353: 187–190 (1993).

Simcox, A. et al., "Imaginal discs can be recovered from cultured embryos mutant for the segment–polarity genes engrailed, naked and patched but not from wingless", *Development*, 107: 715–722 (1991).

Tabata, T. et al., "Hedgehog is a signalling protein with a key role in pattering Drosophila imaginal discs", *Cell*, 76: 89–102 (1994).

Taylor, A. et al., "Contrasting distributions of patched and hedgehog proteins in the Drosophila embryo", *Mechanism of Develop.*, 42: 89–96 (1993).

Thummel, C. et al., "Vectors for Drosophila P–element mediated transformation and tissue culture transfection", *Gene*, 74: 445–456 (1988).

Watson, J., Recombinant DNA, New York, W. H. Freeman and Co., p. 363, (1992).

Wicking, C. et al., "Fine genetic mapping of the gene for nevoid bascal cell carcinoma syndrome"*Genomics*, 22: 505–511 (1994).

SEQUENCE LISTING

<160> NUMBER OF SEQ ID NOS: 6

<210> SEQ ID NO 1
<211> LENGTH: 4391
<212> TYPE: DNA
<213> ORGANISM: human

```
<220> FEATURE:
<221> NAME/KEY: CDS
<222> LOCATION: (297)..(3905)

<400> SEQUENCE: 1
tgcgtctcgg gccatcaatt ccgcctgcgc gcgggaccca ttcctcctcc agccgccacg      60
gactacggcc cacggagcgg gtgaatcccg gcgccgcgcc ccggacccgc agctccctgc     120
actcctccct cccagccgct ttaacaccca caccccacag tctctcccac gcccgcgcct     180
tggcggcccc actgaatccc tacgcggggc ccagcggtac cgggagaccg ggctagccta     240
tgggagcgcc cagataacgc gggttggggg cgccgcgcgcc cccatcccc gccagc atg     299
                                                               Met
                                                                1 act cga tcg ccg ccc ctc aga gag ctg ccc ccg agt tac aca ccc cca       347
Thr Arg Ser Pro Pro Leu Arg Glu Leu Pro Pro Ser Tyr Thr Pro Pro
         5                  10                  15 gct cga acc gca gca ccc cag atc cta gct ggg agc ctg aag gct cca       395
Ala Arg Thr Ala Ala Pro Gln Ile Leu Ala Gly Ser Leu Lys Ala Pro
     20                  25                  30 ctc tgg ctt cgt gct tac ttc cag ggc ctg ctc ttc tct ctg gga tgc       443
Leu Trp Leu Arg Ala Tyr Phe Gln Gly Leu Leu Phe Ser Leu Gly Cys
 35                  40                  45 ggg atc cag aga cat tgt ggc aaa gtg ctc ttt ctg gga ctg ttg gcc       491
Gly Ile Gln Arg His Cys Gly Lys Val Leu Phe Leu Gly Leu Leu Ala
 50                  55                  60                  65 ttt ggg gcc ctg gca tta ggt ctc cgc atg gcc att att gag aca aac       539
Phe Gly Ala Leu Ala Leu Gly Leu Arg Met Ala Ile Ile Glu Thr Asn
             70                  75                  80 ttg gaa cag ctc tgg gta gaa gtg ggc agc cgg gtg agc cag gag ctg       587
Leu Glu Gln Leu Trp Val Glu Val Gly Ser Arg Val Ser Gln Glu Leu
         85                  90                  95 cat tac acc aag gag aag ctg ggg gag gag gct gca tac acc tct cag       635
His Tyr Thr Lys Glu Lys Leu Gly Glu Glu Ala Ala Tyr Thr Ser Gln
    100                 105                 110 atg ctg ata cag acc gca cgc cag gag gga gag aac atc ctc aca ccc       683
Met Leu Ile Gln Thr Ala Arg Gln Glu Gly Glu Asn Ile Leu Thr Pro
115                 120                 125 gaa gca ctt ggc ctc cac ctc cag gca gcc ctc act gcc agt aaa gtc       731
Glu Ala Leu Gly Leu His Leu Gln Ala Ala Leu Thr Ala Ser Lys Val
130                 135                 140                 145 caa gta tca ctc tat ggg aag tcc tgg gat ttg aac aaa atc tgc tac       779
Gln Val Ser Leu Tyr Gly Lys Ser Trp Asp Leu Asn Lys Ile Cys Tyr
                150                 155                 160 aag tca gga gtt ccc ctt att gaa aat gga atg att gag cgg atg att       827
Lys Ser Gly Val Pro Leu Ile Glu Asn Gly Met Ile Glu Arg Met Ile
            165                 170                 175 gag aag ctg ttt ccg tgc gtg atc ctc acc ccc ctc gac tgc ttc tgg       875
Glu Lys Leu Phe Pro Cys Val Ile Leu Thr Pro Leu Asp Cys Phe Trp
        180                 185                 190 gag gga gcc aaa ctc caa ggg ggc tcc gcc tac ctg ccc ggc gcc ccg       923
Glu Gly Ala Lys Leu Gln Gly Gly Ser Ala Tyr Leu Pro Gly Ala Pro
    195                 200                 205 gat atc cag tgg acc aac ctg gat cca gag cag ctg ctg gag gag ctg       971
Asp Ile Gln Trp Thr Asn Leu Asp Pro Glu Gln Leu Leu Glu Glu Leu
210                 215                 220                 225 ggt ccc ttt gcc tcc ctt gag ggc ttc cgg gag ctg cta gac aag gca      1019
Gly Pro Phe Ala Ser Leu Glu Gly Phe Arg Glu Leu Leu Asp Lys Ala
                230                 235                 240 cag gtg ggc cag gcc tac gtg ggg cgg ccc tgt ctg cac cct gat gac      1067
Gln Val Gly Gln Ala Tyr Val Gly Arg Pro Cys Leu His Pro Asp Asp
```

-continued

|  |  |  |  |  |  |  |  |  |  |  |  |  |  |  |  |
|---|---|---|---|---|---|---|---|---|---|---|---|---|---|---|---|
|  |  |  | 245 |  |  |  | 250 |  |  |  | 255 |  |  |  |  |

```
ctc cac tgc cca cct agt gcc ccc aac cat cac agc agg cag gct ccc      1115
Leu His Cys Pro Pro Ser Ala Pro Asn His His Ser Arg Gln Ala Pro
            260                 265                 270 aat gtg gct cac gag ctg agt ggg ggc tgc cat ggc ttc tcc cac aaa      1163
Asn Val Ala His Glu Leu Ser Gly Gly Cys His Gly Phe Ser His Lys
275                 280                 285 ttc atg cac tgg cag gag gaa ttg ctg ctg gga ggc atg gcc aga gac      1211
Phe Met His Trp Gln Glu Glu Leu Leu Leu Gly Gly Met Ala Arg Asp
290                 295                 300                 305 ccc caa gga gag ctg ctg agg gca gag gcc ctg cag agc acc ttc ttg      1259
Pro Gln Gly Glu Leu Leu Arg Ala Glu Ala Leu Gln Ser Thr Phe Leu
                310                 315                 320 ctg atg agt ccc cgc cag ctg tac gag cat ttc cgg ggt gac tat cag      1307
Leu Met Ser Pro Arg Gln Leu Tyr Glu His Phe Arg Gly Asp Tyr Gln
            325                 330                 335 aca cat gac att ggc tgg agt gag gag cag gcc agc aca gtg cta caa      1355
Thr His Asp Ile Gly Trp Ser Glu Glu Gln Ala Ser Thr Val Leu Gln
            340                 345                 350 gcc tgg cag cgg cgc ttt gtg cag ctg gcc cag gag gcc ctg cct gag      1403
Ala Trp Gln Arg Arg Phe Val Gln Leu Ala Gln Glu Ala Leu Pro Glu
355                 360                 365 aac gct tcc cag cag atc cat gcc ttc tcc tcc acc acc ctg gat gac      1451
Asn Ala Ser Gln Gln Ile His Ala Phe Ser Ser Thr Thr Leu Asp Asp
370                 375                 380                 385 atc ctg cat gcg ttc tct gaa gtc agt gct gcc cgt gtg gtg gga ggc      1499
Ile Leu His Ala Phe Ser Glu Val Ser Ala Ala Arg Val Val Gly Gly
                390                 395                 400 tat ctg ctc atg ctg gcc tat gcc tgt gtg acc atg ctg cgg tgg gac      1547
Tyr Leu Leu Met Leu Ala Tyr Ala Cys Val Thr Met Leu Arg Trp Asp
            405                 410                 415 tgc gcc cag tcc cag ggt tcc gtg ggc ctt gcc ggg gta ctg ctg gtg      1595
Cys Ala Gln Ser Gln Gly Ser Val Gly Leu Ala Gly Val Leu Leu Val
            420                 425                 430 gcc ctg gcg gtg gcc tca ggc ctt ggg ctc tgt gcc ctg ctc ggc atc      1643
Ala Leu Ala Val Ala Ser Gly Leu Gly Leu Cys Ala Leu Leu Gly Ile
            435                 440                 445 acc ttc aat gct gcc act acc cag gtg ctg ccc ttc ttg gct ctg gga      1691
Thr Phe Asn Ala Ala Thr Thr Gln Val Leu Pro Phe Leu Ala Leu Gly
450                 455                 460                 465 atc ggc gtg gat gac gta ttc ctg ctg gcg cat gcc ttc aca gag gct      1739
Ile Gly Val Asp Asp Val Phe Leu Leu Ala His Ala Phe Thr Glu Ala
                470                 475                 480 ctg cct ggc acc cct ctc cag gag cgc atg ggc gag tgt ctg cag cgc      1787
Leu Pro Gly Thr Pro Leu Gln Glu Arg Met Gly Glu Cys Leu Gln Arg
            485                 490                 495 acg ggc acc agt gtc gta ctc aca tcc atc aac aac atg gcc gcc ttc      1835
Thr Gly Thr Ser Val Val Leu Thr Ser Ile Asn Asn Met Ala Ala Phe
            500                 505                 510 ctc atg gct gcc ctc gtt ccc atc cct gcg ctg cga gcc ttc tcc cta      1883
Leu Met Ala Ala Leu Val Pro Ile Pro Ala Leu Arg Ala Phe Ser Leu
515                 520                 525 cag gcg gcc ata gtg gtt ggc tgc acc ttt gta gcc gtg atg ctt gtc      1931
Gln Ala Ala Ile Val Val Gly Cys Thr Phe Val Ala Val Met Leu Val
530                 535                 540                 545 ttc cca gcc atc ttc agc ttg gac tta cgg cgg cgc cac tgc cag cgc      1979
Phe Pro Ala Ile Phe Ser Leu Asp Leu Arg Arg Arg His Cys Gln Arg
                550                 555                 560 ctt gat gtg ctc tgc tgc ttc tcc agt ccc tgc tct gct cag gtg att      2027
```

```
                Leu Asp Val Leu Cys Cys Phe Ser Ser Pro Cys Ser Ala Gln Val Ile
                                565                 570                 575 cag atc ctg ccc cag gag ctg ggg gac ggg aca gta cca gtg ggc att           2075
Gln Ile Leu Pro Gln Glu Leu Gly Asp Gly Thr Val Pro Val Gly Ile
            580                 585                 590 gcc cac ctc act gcc aca gtt caa gcc ttt acc cac tgt gag gcc agc           2123
Ala His Leu Thr Ala Thr Val Gln Ala Phe Thr His Cys Glu Ala Ser
        595                 600                 605 agc cag cat gtg gtc acc atc ctg cct ccc caa gcc cac ctg gtg ccc           2171
Ser Gln His Val Val Thr Ile Leu Pro Pro Gln Ala His Leu Val Pro
610                 615                 620                 625 cca cct tct gac cca ctg ggc tct gag ctc ttc agc cct gga ggg tcc           2219
Pro Pro Ser Asp Pro Leu Gly Ser Glu Leu Phe Ser Pro Gly Gly Ser
                630                 635                 640 aca cgg gac ctt cta ggc cag gag gag gag aca agg cag aag gca gcc           2267
Thr Arg Asp Leu Leu Gly Gln Glu Glu Glu Thr Arg Gln Lys Ala Ala
            645                 650                 655 tgc aag tcc ctg ccc tgt gcc cgc tgg aat ctt gcc cat ttc gcc cgc           2315
Cys Lys Ser Leu Pro Cys Ala Arg Trp Asn Leu Ala His Phe Ala Arg
        660                 665                 670 tat cag ttt gcc ccg ttg ctc ctc cag tca cat gcc aag gcc atc gtg           2363
Tyr Gln Phe Ala Pro Leu Leu Leu Gln Ser His Ala Lys Ala Ile Val
675                 680                 685 ctg gtg ctc ttt ggt gct ctt ctg ggc ctg agc ctc tac gga gcc acc           2411
Leu Val Leu Phe Gly Ala Leu Leu Gly Leu Ser Leu Tyr Gly Ala Thr
690                 695                 700                 705 ttg gtg caa gac ggc ctg gcc ctg acg gat gtg gtg cct cgg ggc acc           2459
Leu Val Gln Asp Gly Leu Ala Leu Thr Asp Val Val Pro Arg Gly Thr
                710                 715                 720 aag gag cat gcc ttc ctg agc gcc cag ctc agg tac ttc tcc ctg tac           2507
Lys Glu His Ala Phe Leu Ser Ala Gln Leu Arg Tyr Phe Ser Leu Tyr
            725                 730                 735 gag gtg gcc ctg gtg acc cag ggt ggc ttt gac tac gcc cac tcc caa           2555
Glu Val Ala Leu Val Thr Gln Gly Gly Phe Asp Tyr Ala His Ser Gln
        740                 745                 750 cgc gcc ctc ttt gat ctg cac cag cgc ttc agt tcc ctc aag gcg gtg           2603
Arg Ala Leu Phe Asp Leu His Gln Arg Phe Ser Ser Leu Lys Ala Val
755                 760                 765 ctg ccc cca ccg gcc acc cag gca ccc cgc acc tgg ctg cac tat tac           2651
Leu Pro Pro Pro Ala Thr Gln Ala Pro Arg Thr Trp Leu His Tyr Tyr
770                 775                 780                 785 cgc aac tgg cta cag gga atc cag gct gcc ttt gac cag gac tgg gct           2699
Arg Asn Trp Leu Gln Gly Ile Gln Ala Ala Phe Asp Gln Asp Trp Ala
                790                 795                 800 tct ggg cgc atc acc cgc cac tcg tac cgc aat ggc tct gaa gat ggg           2747
Ser Gly Arg Ile Thr Arg His Ser Tyr Arg Asn Gly Ser Glu Asp Gly
            805                 810                 815 gcc ctg gcc tac aag ctg ctc atc cag act gga gac gcc cag gag cct           2795
Ala Leu Ala Tyr Lys Leu Leu Ile Gln Thr Gly Asp Ala Gln Glu Pro
        820                 825                 830 ctg gat ttc agc cag ctg acc aca agg aag ctg gtg gac aga gag gga           2843
Leu Asp Phe Ser Gln Leu Thr Thr Arg Lys Leu Val Asp Arg Glu Gly
835                 840                 845 ctg att cca ccc gag ctc ttc tac atg ggg ctg acc gtg tgg gtg agc           2891
Leu Ile Pro Pro Glu Leu Phe Tyr Met Gly Leu Thr Val Trp Val Ser
850                 855                 860                 865 agt gac ccc ctg ggt ctg gca gcc tca cag gcc aac ttc tac ccc cca           2939
Ser Asp Pro Leu Gly Leu Ala Ala Ser Gln Ala Asn Phe Tyr Pro Pro
                870                 875                 880
```

-continued

| | |
|---|---|
| cct cct gaa tgg ctg cac gac aaa tac gac acc acg ggg gag aac ctt<br>Pro Pro Glu Trp Leu His Asp Lys Tyr Asp Thr Thr Gly Glu Asn Leu<br>885 890 895 | 2987 |
| cgc atc ccg cca gct cag ccc ttg gag ttt gcc cag ttc ccc ttc ctg<br>Arg Ile Pro Pro Ala Gln Pro Leu Glu Phe Ala Gln Phe Pro Phe Leu<br>900 905 910 | 3035 |
| ctg cgt ggc ctc cag aag act gca gac ttt gtg gag gcc atc gag ggg<br>Leu Arg Gly Leu Gln Lys Thr Ala Asp Phe Val Glu Ala Ile Glu Gly<br>915 920 925 | 3083 |
| gcc cgg gca gca tgc gca gag gcc ggc cag gct ggg gtg cac gcc tac<br>Ala Arg Ala Ala Cys Ala Glu Ala Gly Gln Ala Gly Val His Ala Tyr<br>930 935 940 945 | 3131 |
| ccc agc ggc tcc ccc ttc ctc ttc tgg gaa cag tat ctg ggc ctg cgg<br>Pro Ser Gly Ser Pro Phe Leu Phe Trp Glu Gln Tyr Leu Gly Leu Arg<br>950 955 960 | 3179 |
| cgc tgc ttc ctg ctg gcc gtc tgc atc ctg ctg gtg tgc act ttc ctc<br>Arg Cys Phe Leu Leu Ala Val Cys Ile Leu Leu Val Cys Thr Phe Leu<br>965 970 975 | 3227 |
| gtc tgt gct ctg ctg ctc ctc aac ccc tgg atg gct ggc ctc ata gtg<br>Val Cys Ala Leu Leu Leu Leu Asn Pro Trp Met Ala Gly Leu Ile Val<br>980 985 990 | 3275 |
| ctg gtc ctg gcg atg atg aca gtg gaa ctc ttt ggt atc atg ggt ttc<br>Leu Val Leu Ala Met Met Thr Val Glu Leu Phe Gly Ile Met Gly Phe<br>995 1000 1005 | 3323 |
| ctg ggc atc aag ctg agt gcc atc ccc gtg gtg atc ctt gtg gcc tct<br>Leu Gly Ile Lys Leu Ser Ala Ile Pro Val Val Ile Leu Val Ala Ser<br>1010 1015 1020 1025 | 3371 |
| gta ggc att ggc gtt gag ttc aca gtc cac gtg gct ctg ggc ttc ctg<br>Val Gly Ile Gly Val Glu Phe Thr Val His Val Ala Leu Gly Phe Leu<br>1030 1035 1040 | 3419 |
| acc acc cag ggc agc cgg aac ctg cgg gcc gcc cat gcc ctt gag cac<br>Thr Thr Gln Gly Ser Arg Asn Leu Arg Ala Ala His Ala Leu Glu His<br>1045 1050 1055 | 3467 |
| aca ttt gcc ccc gtg acc gat ggg gcc atc tcc aca ttg ctg ggt ctg<br>Thr Phe Ala Pro Val Thr Asp Gly Ala Ile Ser Thr Leu Leu Gly Leu<br>1060 1065 1070 | 3515 |
| ctc atg ctt gct ggt tcc cac ttt gac ttc att gta agg tac ttc ttt<br>Leu Met Leu Ala Gly Ser His Phe Asp Phe Ile Val Arg Tyr Phe Phe<br>1075 1080 1085 | 3563 |
| gcg gcg ctg aca gtg ctc acg ctc ctg ggc ctc ctc cat gga ctc gtg<br>Ala Ala Leu Thr Val Leu Thr Leu Leu Gly Leu Leu His Gly Leu Val<br>1090 1095 1100 1105 | 3611 |
| ctg ctg cct gtg ctg ctg tcc atc ctg ggc ccg ccg cca gag gtg ata<br>Leu Leu Pro Val Leu Leu Ser Ile Leu Gly Pro Pro Pro Glu Val Ile<br>1110 1115 1120 | 3659 |
| cag atg tac aag gaa agc cca gag atc ctg agt cca cca gct cca cag<br>Gln Met Tyr Lys Glu Ser Pro Glu Ile Leu Ser Pro Pro Ala Pro Gln<br>1125 1130 1135 | 3707 |
| gga ggc ggg ctt agg tgg ggg gca tcc tcc tcc ctg ccc cag agc ttt<br>Gly Gly Gly Leu Arg Trp Gly Ala Ser Ser Ser Leu Pro Gln Ser Phe<br>1140 1145 1150 | 3755 |
| gcc aga gtg act acc tcc atg acc gtg gcc atc cac cca ccc ccc ctg<br>Ala Arg Val Thr Thr Ser Met Thr Val Ala Ile His Pro Pro Pro Leu<br>1155 1160 1165 | 3803 |
| cct ggt gcc tac atc cat cca gcc cct gat gag ccc cct tgg tcc cct<br>Pro Gly Ala Tyr Ile His Pro Ala Pro Asp Glu Pro Pro Trp Ser Pro<br>1170 1175 1180 1185 | 3851 |
| gct gcc act agc tct ggc aac ctc agt tcc agg gga cca ggt cca gcc<br>Ala Ala Thr Ser Ser Gly Asn Leu Ser Ser Arg Gly Pro Gly Pro Ala<br>1190 1195 1200 | 3899 |

-continued

```
act ggg tgaaagagca gctgaagcac agagaccatg tgtggggcgt gtggggtcac      3955
Thr Gly tgggaagcac tgggtctggt gttagacgca ggatggaccc ctggagggcc ctgctgctgc    4015
tgcatccctt ctcccgaccc agctgtcatg ggcctccctg atatccatac agaacagcca    4075
ccgatttgca catccaggcc tgtgtgagcc tgtatctgtg tcacttgaga gtgaaagctg    4135
gcacttgggg ctgcagtgca gccctgtccc ccttcccacc ccacaccact gcctgcccag    4195
ctgaccaagc tgagggacc ctccagcacc cttccgtctg gtgactcctg ggcaggctct     4255
ccatatccct gcccacctcc taccacatcc attatttata tgaaaatgtc tattttgta    4315 gtagacatac atgttagcta tgatgaaagt tttatttttt aaagaatgaa atatattcta    4375
tgtgaactct cgtgcc                                                    4391
```

<210> SEQ ID NO 2
<211> LENGTH: 1203
<212> TYPE: PRT
<213> ORGANISM: human

<400> SEQUENCE: 2

```
Met Thr Arg Ser Pro Pro Leu Arg Glu Leu Pro Pro Ser Tyr Thr Pro
 1               5                  10                  15

Pro Ala Arg Thr Ala Ala Pro Gln Ile Leu Ala Gly Ser Leu Lys Ala
                20                  25                  30

Pro Leu Trp Leu Arg Ala Tyr Phe Gln Gly Leu Leu Phe Ser Leu Gly
            35                  40                  45

Cys Gly Ile Gln Arg His Cys Gly Lys Val Leu Phe Leu Gly Leu Leu
        50                  55                  60

Ala Phe Gly Ala Leu Ala Leu Gly Leu Arg Met Ala Ile Ile Glu Thr
    65                  70                  75                  80

Asn Leu Glu Gln Leu Trp Val Glu Val Gly Ser Arg Val Ser Gln Glu
                85                  90                  95

Leu His Tyr Thr Lys Glu Lys Leu Gly Glu Glu Ala Ala Tyr Thr Ser
               100                 105                 110

Gln Met Leu Ile Gln Thr Ala Arg Gln Glu Gly Glu Asn Ile Leu Thr
           115                 120                 125

Pro Glu Ala Leu Gly Leu His Leu Gln Ala Ala Leu Thr Ala Ser Lys
       130                 135                 140

Val Gln Val Ser Leu Tyr Gly Lys Ser Trp Asp Leu Asn Lys Ile Cys
   145                 150                 155                 160

Tyr Lys Ser Gly Val Pro Leu Ile Glu Asn Gly Met Ile Glu Arg Met
               165                 170                 175

Ile Glu Lys Leu Phe Pro Cys Val Ile Leu Thr Pro Leu Asp Cys Phe
           180                 185                 190

Trp Glu Gly Ala Lys Leu Gln Gly Gly Ser Ala Tyr Leu Pro Gly Arg
       195                 200                 205

Pro Asp Ile Gln Trp Thr Asn Leu Asp Pro Glu Gln Leu Leu Glu Glu
   210                 215                 220

Leu Gly Pro Phe Ala Ser Leu Glu Gly Phe Arg Glu Leu Leu Asp Lys
225                 230                 235                 240

Ala Gln Val Gly Gln Ala Tyr Val Gly Arg Pro Cys Leu His Pro Asp
               245                 250                 255

Asp Leu His Cys Pro Pro Ser Ala Pro Asn His His Ser Arg Gln Ala
           260                 265                 270
```

-continued

```
Pro Asn Val Ala His Glu Leu Ser Gly Gly Cys His Gly Phe Ser His
        275                 280                 285

Lys Phe Met His Trp Gln Glu Glu Leu Leu Gly Gly Met Ala Arg
        290                 295                 300

Asp Pro Gln Gly Glu Leu Leu Arg Ala Glu Ala Leu Gln Ser Thr Phe
305                 310                 315                 320

Leu Leu Met Ser Pro Arg Gln Leu Tyr Glu His Phe Arg Gly Asp Tyr
                325                 330                 335

Gln Thr His Asp Ile Gly Trp Ser Glu Glu Gln Ala Ser Thr Val Leu
                340                 345                 350

Gln Ala Trp Gln Arg Arg Phe Val Gln Leu Ala Gln Glu Ala Leu Pro
                355                 360                 365

Glu Asn Ala Ser Gln Gln Ile His Ala Phe Ser Ser Thr Thr Leu Asp
        370                 375                 380

Asp Ile Leu His Ala Phe Ser Glu Val Ser Ala Ala Arg Val Val Gly
385                 390                 395                 400

Gly Tyr Leu Leu Met Leu Ala Tyr Ala Cys Val Thr Met Leu Arg Trp
                405                 410                 415

Asp Cys Ala Gln Ser Gln Gly Ser Val Gly Leu Ala Gly Val Leu Leu
                420                 425                 430

Val Ala Leu Ala Val Ala Ser Gly Leu Gly Leu Cys Ala Leu Leu Gly
                435                 440                 445

Ile Thr Phe Asn Ala Ala Thr Thr Gln Val Leu Pro Phe Leu Ala Leu
        450                 455                 460

Gly Ile Gly Val Asp Asp Val Phe Leu Leu Ala His Ala Phe Thr Glu
465                 470                 475                 480

Ala Leu Pro Gly Thr Pro Leu Gln Glu Arg Met Gly Glu Cys Leu Gln
                485                 490                 495

Arg Thr Gly Thr Ser Val Val Leu Thr Ser Ile Asn Asn Met Ala Ala
                500                 505                 510

Phe Leu Met Ala Ala Leu Val Pro Ile Pro Ala Leu Arg Ala Phe Ser
        515                 520                 525

Leu Gln Ala Ala Ile Val Val Gly Cys Thr Phe Val Ala Val Met Leu
        530                 535                 540

Val Phe Pro Ala Ile Phe Ser Leu Asp Leu Arg Arg Arg His Cys Gln
545                 550                 555                 560

Arg Leu Asp Val Leu Cys Cys Phe Ser Ser Pro Cys Ser Ala Gln Val
                565                 570                 575

Ile Gln Ile Leu Pro Gln Glu Leu Gly Asp Gly Thr Val Pro Val Gly
                580                 585                 590

Ile Ala His Leu Thr Ala Thr Val Gln Ala Phe Thr His Cys Glu Ala
        595                 600                 605

Ser Ser Gln His Val Val Thr Ile Leu Pro Pro Gln Ala His Leu Val
        610                 615                 620

Pro Pro Pro Ser Asp Pro Leu Gly Ser Glu Leu Phe Ser Pro Gly Gly
625                 630                 635                 640

Ser Thr Arg Asp Leu Leu Gly Gln Glu Glu Thr Arg Gln Lys Ala
                645                 650                 655

Ala Cys Lys Ser Leu Pro Cys Ala Arg Trp Asn Leu Ala His Phe Ala
                660                 665                 670

Arg Tyr Gln Phe Ala Pro Leu Leu Leu Gln Ser His Ala Lys Ala Ile
                675                 680                 685

Val Leu Val Leu Phe Gly Ala Leu Leu Gly Leu Ser Leu Tyr Gly Ala
```

-continued

```
            690                  695                  700
Thr Leu Val Gln Asp Gly Leu Ala Leu Thr Asp Val Val Pro Arg Gly
705                 710                  715                  720
Thr Lys Glu His Ala Phe Leu Ser Ala Gln Leu Arg Tyr Phe Ser Leu
                725                  730                  735
Tyr Glu Val Ala Leu Val Thr Gln Gly Gly Phe Asp Tyr Ala His Ser
                740                  745                  750
Gln Arg Ala Leu Phe Asp Leu His Gln Arg Phe Ser Ser Leu Lys Ala
                755                  760                  765
Val Leu Pro Pro Ala Thr Gln Ala Pro Arg Thr Trp Leu His Tyr
770                 775                  780
Tyr Arg Asn Trp Leu Gln Gly Ile Gln Ala Ala Phe Asp Gln Asp Trp
785                 790                  795                  800
Ala Ser Gly Arg Ile Thr Arg His Ser Tyr Arg Asn Gly Ser Glu Asp
                805                  810                  815
Gly Ala Leu Ala Tyr Lys Leu Leu Ile Gln Thr Gly Asp Ala Gln Glu
                820                  825                  830
Pro Leu Asp Phe Ser Gln Leu Thr Thr Arg Lys Leu Val Asp Arg Glu
                835                  840                  845
Gly Leu Ile Pro Pro Glu Leu Phe Tyr Met Gly Leu Thr Val Trp Val
850                 855                  860
Ser Ser Asp Pro Leu Gly Leu Ala Ala Ser Gln Ala Asn Phe Tyr Pro
865                 870                  875                  880
Pro Pro Pro Glu Trp Leu His Asp Lys Tyr Asp Thr Thr Gly Glu Asn
                885                  890                  895
Leu Arg Ile Pro Pro Ala Gln Pro Leu Glu Phe Ala Gln Phe Pro Phe
                900                  905                  910
Leu Leu Arg Gly Leu Gln Lys Thr Ala Asp Phe Val Glu Ala Ile Glu
                915                  920                  925
Gly Ala Arg Ala Ala Cys Ala Glu Ala Gly Gln Ala Gly Val His Ala
                930                  935                  940
Tyr Pro Ser Gly Ser Pro Phe Leu Phe Trp Glu Gln Tyr Leu Gly Leu
945                 950                  955                  960
Arg Arg Cys Phe Leu Leu Ala Val Cys Ile Leu Leu Val Cys Thr Phe
                965                  970                  975
Leu Val Cys Ala Leu Leu Leu Asn Pro Trp Met Ala Gly Leu Ile
                980                  985                  990
Val Leu Val Leu Ala Met Met Thr Val Glu Leu Phe Gly Ile Met Gly
                995                 1000                 1005
Phe Leu Gly Ile Lys Leu Ser Ala Ile Pro Val Val Ile Leu Val Ala
                1010                 1015                 1020
Ser Val Gly Ile Gly Val Glu Phe Thr Val His Val Ala Leu Gly Phe
025                 1030                 1035                 1040
Leu Thr Thr Gln Gly Ser Arg Asn Leu Arg Ala Ala His Ala Leu Glu
                1045                 1050                 1055
His Thr Phe Ala Pro Val Thr Asp Gly Ala Ile Ser Thr Leu Leu Gly
                1060                 1065                 1070
Leu Leu Met Leu Ala Gly Ser His Phe Asp Phe Ile Val Arg Tyr Phe
                1075                 1080                 1085
Phe Ala Ala Leu Thr Val Leu Thr Leu Leu Gly Leu Leu His Gly Leu
                1090                 1095                 1100
Val Leu Leu Pro Val Leu Leu Ser Ile Leu Gly Pro Pro Pro Glu Val
105                 1110                 1115                 1120
```

```
Ile Gln Met Tyr Lys Glu Ser Pro Glu Ile Leu Ser Pro Pro Ala Pro
            1125            1130            1135

Gln Gly Gly Gly Leu Arg Trp Gly Ala Ser Ser Ser Leu Pro Gln Ser
        1140            1145            1150

Phe Ala Arg Val Thr Thr Ser Met Thr Val Ala Ile His Pro Pro Pro
        1155            1160            1165

Leu Pro Gly Ala Tyr Ile His Pro Ala Pro Asp Glu Pro Pro Trp Ser
    1170            1175            1180

Pro Ala Ala Thr Ser Ser Gly Asn Leu Ser Ser Arg Gly Pro Gly Pro
185             1190            1195            1200

Ala Thr Gly

<210> SEQ ID NO 3
<211> LENGTH: 20
<212> TYPE: DNA
<213> ORGANISM: primer

<400> SEQUENCE: 3
caaactccaa ggggctctg                                               20

<210> SEQ ID NO 4
<211> LENGTH: 20
<212> TYPE: DNA
<213> ORGANISM: primer

<400> SEQUENCE: 4
cacaaagccc aagacctgag                                              20

<210> SEQ ID NO 5
<211> LENGTH: 20
<212> TYPE: DNA
<213> ORGANISM: primer
<220> FEATURE:
<223> OTHER INFORMATION: bases designated as "n" may be A, T, C, G
      or other

<400> SEQUENCE: 5
tggaattctt gggtngtngc                                              20

<210> SEQ ID NO 6
<211> LENGTH: 17
<212> TYPE: DNA
<213> ORGANISM: primer

<400> SEQUENCE: 6
gaytgyttyt gggargg                                                 17
```

HUMAN PATCHED GENES AND PROTEINS, AND USES RELATED THERETO

RELATED APPLICATIONS

The present application is a continuation-in-part of provisional application U.S. Ser. No. 60/067,940, filed Dec. 8, 1997, the specification of which is incorporated herein by reference.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

The origin of the nervous system in all vertebrates can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, *Principles in Neural Science* (3rd), eds. Kandel, Schwartz and Jessell, Elsevier Science Publishing Company: NY, 1991; and *Developmental Biology* (3rd), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identify of cell types is controlled, in part, by signals from two midline cell groups, the notochord and floor plate, that induce neural plate cells to differentiate into floor plate, motor neurons, and other ventral neuronal types (van Straaten et al. (1988) *Anat. Embryol.* 177:317–324; Placzek et al. (1993) *Development* 117:205–218; Yamada et al. (1991) *Cell* 64:035–647; and Hatta et al. (1991) *Nature* 350:339–341). In addition, signals from the floor plate are responsible for the orientation and direction of commissural neuron outgrowth (Placzek, M. et al., (1990) *Development* 110: 19–30). Besides patterning the neural tube, the notochord and floorplate are also responsible for producing signals which control the patterning of the somites by inhibiting differentiation of dorsal somite derivatives in the ventral regions (Brand-Saberi, B. et al., (1993) *Anat. Embryol.* 188: 239–245; Porquie, O. et al., (1993) *Proc. Natl. Acad. Sci. USA* 90: 5242–5246).

Another important signaling center exists in the posterior mesenchyme of developing limb buds, called the Zone of Polarizing Activity, or "ZPA". When tissue from the posterior region of the limb bud is grafted to the anterior border of a second limb bud, the resultant limb will develop with additional digits in a mirror-image sequence along the anteroposterior axis (Saunders and Gasseling, (1968) *Epithelial-Mesenchymal Interaction*, pp. 78–97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) *Theor. Biol.* 25:1–47). This is supported by the finding that the extent of digit duplication is proportional to the number of implanted ZPA cells (Tickle, (1981) *Nature* 254:199–202).

Although the existence of inductive signals in the ZPA has been known for years, the molecular identities of these signals are only now beginning to be elucidated. An important step forward has been the discovery that the secreted protein Sonic hedgehog (Shh) is produced in several tissues with organizing properties, including notochord, floor plate and ZPA (Echelard et al. (1993), *Cell* 75: 1417–1430; Bitgood, M. J. and A. P. McMahon (1995) *Dev. Biol.* 172:126–38). Misexpressing Shh mimics the inductive effects on ectopic notochord in the neural tube and somites (Echelard et al. (1993) supra) and also mimics ZPA function in the limb bud (Riddle et al. (1993) *Cell* 75:1401–16; Chang et al. (1994) *Development* 120: 3339–53).

The vertebrate family of hedgehog genes includes at least four members, e.g., paralogs of the single drosophila hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

SUMMARY OF THE INVENTION

The present invention relates to the discovery of a new member of the hedgehog receptor family, referred to herein as human ptc-2 (for patched-2 protein). The human ptc-2 polypeptides of the present invention include polypeptides which bind the products of the hedgehog gene family. Hedgehog family members are known for their broad involvement in the formation and maintenance of ordered spatial arrangements of differentiated tissues in vertebrates, both adult and embryonic, and can be used to generate and/or maintain an array of different vertebrate tissue both in vitro and in vivo.

In general, the invention features isolated ptc-2 polypeptides, preferably substantially pure preparations of the subject ptc-2 polypeptides. The invention also provides recombinantly produced human ptc-2 polypeptides.

In one embodiment, the polypeptide is identical with or homologous to the ptc-2 polypeptide represented in SEQ ID No: 2.

The ptc-2 polypeptide can comprise a full length protein, or it may include only a hedgehog-binding portion thereof, or it may be of arbitrary sizes, e.g., at least 5, 10, 25, 50, 100, 150 or 200 amino acids in length. In preferred embodiments, the ptc-2 polypeptide includes a sufficient portion of the extracellular ligand binding domain to be able to specifically bind to a hedgehog ligand. Truncated forms of the protein include, but are not limited to, soluble ligand binding domain fragments.

In yet another embodiment, the invention features nucleic acids encoding ptc-2 polypeptides, which have the ability to modulate, e.g., either mimic or antagonize, at least a portion of the activity of a wild-type ptc-2 polypeptide. Exemplary ptc-2-encoding nucleic acid sequences are represented by SEQ ID No: 1. In another embodiment, the nucleic acids of the present invention include coding sequences which hybridize under stringent conditions with all or a portion of the coding sequences designated in SEQ ID No: 1.

Furthermore, in certain preferred embodiments, the subject ptc-2 nucleic acids will include a transcriptional regulatory sequence, e.g. at least one of a transcriptional promoter or transcriptional enhancer sequence, which regulatory sequence is operably linked to the ptc-2 gene sequences. Such regulatory sequences can be used in to render the ptc-2 gene sequences suitable for use as an expression vector. The transcriptional regulatory sequence can be from a ptc-2 gene, or from a heterologous gene.

This invention also contemplates the cells transfected with said expression vector whether prokaryotic or eukaryotic and a method for producing ptc-2 proteins by employing said expression vectors.

In still other embodiments, the subject invention provides a gene activation construct, wherein the gene activation construct is deigned to recombine with a genomic ptc-2 gene in a cell to provide, e.g., by heterologous recombination, a heterologous transcriptional regulatory sequence operatively linked to a coding sequence of a genomic ptc-2 gene. Cells having genomic ptc-2 genes modified by gene activation constructs are also specifically contemplated.

A still further aspect of the present invention features antibodies and antibody preparations specifically reactive with an epitope of the ptc-2 immunogen.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequences of any one or more of SEQ ID No: 1, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a ptc-2 protein, such as for detecting in a sample of cells isolated from a patient, a level of a nucleic acid encoding a ptc-2 protein; e.g. measuring a ptc-2 mRNA level in a cell, or determining whether a genomic ptc-2 gene has been mutated or deleted. These so-called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject ptc-2 proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between a hedgehog protein and a ptc-2 polypeptide receptor. An exemplary method includes the steps of (a) forming a reaction mixture including: (i) a hedgehog polypeptide, (ii) a ptc-2 polypeptide, and (iii) a test compound; and (b) detecting interaction of the hedgehog and ptc-2 polypeptides. A statistically significant change (potentiation or inhibition) in the interaction of the hedgehog and ptc-2 polypeptides in the presence of the test compound, relative to the interaction in the absence of the test compound, indicates a potential agonist (mimetic or potentiator) or antagonist (inhibitor) of hedgehog bioactivity for the test compound. The reaction mixture can be a cell-free protein preparation, e.g., a reconstituted protein mixture or a cell lysate, or it can be a recombinant cell including a heterologous nucleic acid recombinantly expressing the ptc-2 polypeptide.

In preferred embodiments, the step of detecting interaction of the hedgehog and ptc-2 polypeptides is a competitive binding assay. In other preferred embodiments, the step of detecting interaction of the hedgehog and ptc-2 polypeptides involves detecting, in a cell-based assay, change(s) in the level of an intracellular second messenger responsive to signaling mediated by the ptc-2 polypeptide. In still another preferred embodiment, the step of detecting interaction of the hedgehog and ptc-2 polypeptides comprises detecting, in a cell-based assay, change(s) in the level of expression of a gene controlled by a transcriptional regulatory sequence responsive to signaling by the ptc-2 polypeptide.

In preferred embodiments, the steps of the assay are repeated for a variegated library of at least 100 different test compounds, more preferably at least $10^3$, $10^4$ or $10^5$ different test compounds. The test compound can be, e.g., a peptide, a nucleic acid, a carbohydrate, a small organic molecule, or natural product extract (or fraction thereof).

The present invention further contemplates the pharmaceutical formulation of one or more agents identified in such drug screening assays.

In other embodiments, the present invention provides a molecule, preferably a small organic molecule, which binds to ptc-2 and either mimics or antagonizes hedgehog-induced signaling in cells expressing ptc-2.

Yet another aspect of the present invention concerns a method for modulating one or more of growth, differentiation, or survival of a cell by modulating ptc-2 bioactivity, e.g., by potentiating or disrupting certain protein-protein interactions. In general, whether carried out in vivo, in vitro, or in situ, the method comprises treating the cell with an effective amount of a ptc-2 therapeutic so as to alter, relative to the cell in the absence of treatment, at least one of (i) rate of growth, (ii) differentiation, or (iii) survival of the cell. Accordingly, the method can be carried out with ptc-2 therapeutics such as peptide and peptidomimetics or other molecules identified in the above-referenced drug screens which agonize or antagonize the effects of signaling from a ptc-2 protein or ligand binding of a ptc-2 protein, e.g., a hedgehog protein. Other ptc-2 therapeutics include antisense constructs for inhibiting expression of ptc-2 proteins, dominant negative mutants of ptc-2 proteins which competitively inhibit ligand interactions upstream and signal transduction downstream of the wild-type ptc-2 protein, and gene therapy constructs including gene activation constructs.

In one embodiment, the subject method of modulating ptc-2 bioactivity can be used in the treatment of testicular cells, so as to modulate spermatogenesis. In another embodiment, the subject method is used to modulate osteogenesis, comprising the treatment of osteogenic cells with an agent that modulates ptc-2 bioactivity. Likewise, where the treated cell is a chondrogenic cell, the present method is used to modulate chondrogenesis. In still, another embodiment, the subject method can be used to modulate the differentiation of a neuronal cell, to maintain a neuronal cell in a differentiated state, and/or to enhance the survival of a neuronal cell, e.g., to prevent apoptosis or other forms of cell death. For instance the present method can be used to affect the differentiation of neuronal cells such as motor neurons, cholinergic neurons, dopaminergic neurons, serotonergic neurons, and peptidergic neurons.

Another aspect of the present invention provides a method of determining if a subject, e.g. an animal patient, is at risk for a disorder characterized by unwanted cell proliferation or aberrant control of differentiation or apoptosis. The method includes detecting, in a tissue of the subject, the presence or absence of a genetic lesion characterized by at least one of (i) a mutation of a gene encoding a ptc-2 protein; or (ii) the mis-expression of a ptc-2 gene. In preferred embodiments, detecting the genetic lesion includes ascertaining the existence of at least one of: a deletion of one or more nucleotides from a ptc-2 gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble ptc-2 protein.

For example, detecting the genetic lesion can include (i) providing a probe/primer including an oligonucleotide containing a region of nucleotide sequence which hybridizes to a sense or antisense sequence of a ptc-2 gene or naturally occurring mutants thereof, or 5' or 3' flanking sequences naturally associated with the ptc-2 gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the ptc-2 gene and, optionally, of the flanking nucleic acid sequences. For instance, the probe/primer can be employed in a polymerase chain reaction (PCR) or in a ligation chain reaction (LCR). In alternate embodiments, the level of a ptc-2 protein is detected in an immunoassay using an antibody which is specifically immunoreactive with the ptc-2 protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

DETAILED DESCRIPTION OF THE INVENTION

Of particular importance in the development and maintenance of tissue in vertebrate animals is a type of extracellular communication called induction, which occurs between neighboring cell layers and tissues. In inductive interactions, chemical signals secreted by one cell population influence the developmental fate of a second cell population. Typically, cells responding to the inductive signals are diverted from one cell fate to another, neither of which is the same as the fate of the signaling cells.

Inductive signals are key regulatory proteins that function in vertebrate pattern formation, and are present in important signaling centers known to operate embryonically, for example, to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the Zone of Polarizing Activity or ZPA) operates as a signaling center by secreting a morphogen which ultimately produces the correct patterning of the developing limbs.

The regulation of hedgehog protein signaling is an important mechanism for developmental control. The present invention concerns the discovery of a new member of the hedgehog receptor family, referred to herein as "patched-2" or "ptc-2".

The sequence of an exemplary human ptc-2 gene (cf, SEQ ID No. 1) indicates it encodes a serpentine membrane protein. The ptc-2 proteins, through their ability to bind to hedgehog proteins, are apparently capable of modulating hedgehog signaling. The ptc-2 proteins can function as a hedgehog receptor (or subunit thereof). Thus, the ptc-2 polypeptides of the present invention may affect a number of hedgehog-mediated biological activities including: an ability to modulate proliferation, survival and/or differentiation of mesodermally-derived tissue, such as tissue derived from dorsal mesoderm, cartilage and tissue involved in spermatogenesis; the ability to modulate proliferation, survival and/or differentiation of ectodermally-derived tissue, such as tissue derived from the epidermis, neural tube, neural crest, or head mesenchyme; the ability to modulate proliferation, survival and/or differentiation of endodermally-derived tissue, such as tissue derived from the primitive gut.

Accordingly, certain aspects of the present invention relate to nucleic acids encoding ptc-2 polypeptides, the ptc-2 polypeptides themselves (including various fragments), antibodies immunoreactive with ptc-2 proteins, and preparations of such compositions. Moreover, the present invention provides diagnostic and therapeutic assays and reagents for detecting and treating disorders involving, for example, aberrant expression (or loss thereof) of ptc-2, ptc-2 ligands (particularly hedgehog proteins), or signal transducers thereof.

In addition, drug discovery assays are provided for identifying agents which can modulate the biological function of ptc-2 proteins, such as by altering the binding of ptc-2 molecules to hedgehog proteins or other extracellular/matrix factors, or the ability of the bound ptc-2 protein to transduce hedgehog signals. Such agents can be useful therapeutically to alter the growth, maintenance and/or differentiation of a tissue, particularly a mesodermally-derived tissue, such cartilage, tissue involved in spermatogenesis and tissue derived from dorsal mesoderm; ectodermally-derived tissue, such as tissue derived from the epidermis, neural tube, neural crest, or head mesenchyme; endodermally-derived tissue, such as tissue derived from the primitive gut. Other aspects of the invention are described below or will be apparent to those skilled in the art in light of the present disclosure.

For convenience, certain terms employed in the specification and appended claims are collected here.

The term "human ptc-2" polypeptide refers to polypeptides characterized at least in part by being identical or sharing a degree of sequence homology with all or a portion of the a ptc-2 polypeptide represented in SEQ ID No: 2.

A "glycosylated" ptc-2 polypeptide is an ptc-2 polypeptide having a covalent linkage with a glycosyl group (e.g. a derivatized with a carbohydrate). For instance, the ptc-2 protein can be glycosylated on an existing residue, or can be mutated to preclude carbohydrate attachment, or can be mutated to provide new glycosylation sites, such as for N-linked or O-linked glycosylation.

As used herein, the term "vertebrate hedgehog protein" refers to vertebrate inter-cellular signaling molecules related to the Drosophila hedgehog protein. Three of the vertebrate hedgehog proteins, Desert hedgehog (Dhh), Sonic hedgehog (Shh) and Indian hedgehog (Ihh), apparently exist in all vertebrates, including amphibians, fish, birds, and mammals. Other members of this family, such as Banded hedgehog, Cephalic hedgehog, tiggy-winkle hedgehog, and echidna hedgehog have been so far identified in fish and/or amphibians. Exemplary hedgehog polypeptides are described in PCT applications WO96/17924, WO96/16668, WO95/18856.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a ptc-2 polypeptide, including both exon and (optionally) intron sequences. A "recombinant gene" refers to nucleic acid encoding a ptc-2 polypeptide and comprising ptc-2-encoding exon sequences, though it may optionally include intron sequences which are derived from, for example, a chromosomal ptc-2 gene or from an unrelated chromosomal gene. Exemplary recombinant genes encoding the subject ptc-2 polypeptide are represented in the appended Sequence Listing. The term "intron" refers to a DNA sequence present in a given ptc-2 gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a ptc-2 polypeptide or, where anti-sense expression occurs from the transferred gene, the expression of a naturally-occurring form of the ptc-2 protein is disrupted.

As used herein, the term "specifically hybridizes" refers to the ability of a nucleic acid probe/primer of the invention to hybridize to at least 15 consecutive nucleotides of a ptc-2 gene, such as the ptc-2 sequence designated in SEQ ID No: 1, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a ptc-2 protein, as defined herein.

An "effective amount" of a hedgehog polypeptide, or a bioactive fragment thereof, with respect to the subject method of treatment, refers to an amount of agonist or antagonist in a preparation which, when applied as part of a desired dosage regimen, provides modulation of growth, differentiation or survival of cells, e.g., modulation of spermatogenesis, neuronal differentiation, or skeletogenesis, e.g., osteogenesis, chondrogenesis, or limb patterning.

As used herein, "phenotype" refers to the entire physical, biochemical, and physiological makeup of a cell, e.g., having any one trait or any group of traits.

The terms "induction" or "induce", as relating to the biological activity of a hedgehog protein, refers generally to the process or act of causing to occur a specific effect on the phenotype of cell. Such effect can be in the form of causing a change in the phenotype, e.g., differentiation to another cell phenotype, or can be in the form of maintaining the cell in a particular cell, e.g., preventing dedifferentation or promoting survival of a cell.

A "patient" or "subject" to be treated can mean either a human or non-human animal.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant ptc-2 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of ptc-2 genes.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neuronal or hematopoietic origin. The term also covers so-called "leaky" promoters, which regulate expression of a selected DNA primarily in one tissue, but can cause at least low level expression in other tissues as well.

As used herein, the term "target tissue" refers to connective tissue, cartilage, bone tissue or limb tissue, which is either present in an animal, e.g., a mammal, e.g., a human or is present in vitro culture, e.g., a cell culture.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a ptc-2 polypeptide" may thus refer to one or more genes within a particular individual. Moreover, certain differences in nucleotide sequences may exist between individuals of the same species, which are called alleles. Such allelic differences may or may not result in differences in amino acid sequence of the encoded polypeptide yet still encode a protein with the same biological activity.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a ptc-2 sequence of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding a ptc-2 polypeptide with a second amino acid sequence defining a domain (e.g. polypeptide portion) foreign to and not substantially homologous with any domain of a ptc-2 protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-ptc-2-Y, wherein ptc-2 represents a portion of the fusion protein which is derived from a ptc-2 protein, and X and Y are, independently, absent or represent amino acid sequences which are not related to a ptc-2 sequences in an organism.

As used herein, a "reporter gene construct" is a nucleic acid that includes a "reporter gene" operatively linked to a transcriptional regulatory sequences. Transcription of the reporter gene is controlled by these sequences. The activity of at least one or more of these control sequences is directly or indirectly regulated by a signal transduction pathway involving a phospholipase, e.g., is directly or indirectly regulated by a second messenger produced by the phospholipase activity. The transcriptional regulatory sequences can include a promoter and other regulatory regions, such as enhancer sequences, that modulate the activity of the promoter, or regulatory sequences that modulate the activity or efficiency of the RNA polymerase that recognizes the promoter, or regulatory sequences that are recognized by effector molecules, including those that are specifically induced upon activation of a phospholipase. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter the stability or rate of translation of the resulting mRNA in response to second messages, thereby altering the amount of reporter gene product.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding a ptc-2 polypeptide preferably includes no more than 10 kilobases (kb) of nucleic acid sequence which naturally immediately flanks the ptc-2 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding ptc-2 polypeptides, and/or equivalents of such nucleic acids. The term nucleic acid as used herein is intended to include fragments as equivalents. The term equivalent is understood to include nucleotide sequences encoding functionally equivalent ptc-2 polypeptides or functionally equivalent peptides having an activity of a ptc-2 protein such as described herein. Equivalent nucleotide sequences will include sequences that differ by one or more nucleotide substitutions, additions or deletions, such as allelic variants; and will, therefore, include sequences that differ from the nucleotide sequence of the human ptc-2 coding sequence of SEQ ID No: 1 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequences represented in SEQ ID No: 1.

Moreover, it will be generally appreciated that, under certain circumstances, it may be advantageous to provide homologs of a ptc-2 polypeptide which function in a limited capacity as one of either an agonist (e.g., mimics or potentiates a bioactivity of the wild-type ptc-2 protein) or an antagonist (e.g., inhibits a bioactivity of the wild-type ptc-2 protein), in order to promote or inhibit only a subset of the biological activities of the naturally-occurring form of the protein. Thus, specific biological effects can be elicited by treatment with a homolog of limited function. For example, truncated forms of the patched-2 protein, e.g., soluble fragments of an extracellular domain, can be provided to competitively inhibit ligand (hedgehog) binding to the wild-type ptc-2 protein.

Homologs of the subject ptc-2 protein can be generated by mutagenesis, such as by discrete point mutation(s), or by truncation. For instance, mutation can give rise to homologs which retain substantially the same, or merely a subset, of the biological activity of the ptc-2 polypeptide from which it was derived. Alternatively, antagonistic forms of the protein can be generated which are able to inhibit the function of the naturally occurring form of the protein, such as by competitively binding to hedgehog proteins and competing with wild-type ptc-2, or binding to other patched-2 proteins (such as subunits of a hedgehog receptor) to form unresponsive hedgehog receptor complexes. Thus, the ptc-2 protein and homologs thereof provided by the subject invention may be either positive or negative regulators of cell growth, death and/or differentiation.

In general, polypeptides referred to herein as having an activity of a ptc-2 protein (e.g., are "bioactive") are defined as polypeptides which include an amino acid sequence corresponding (e.g., identical or homologous) to all or a portion of the amino acid sequences of the ptc-2 protein shown in SEQ ID No: 2, and which agonize or antagonize all or a portion of the biological/biochemical activities of a naturally occurring ptc-2 protein. Examples of such biological activity includes the ability to bind with high affinity hedgehog proteins. The bioactivity of certain embodiments of the subject ptc-2 polypeptides can be characterized in terms of an ability to promote differentiation and/or maintenance of cells and tissue from mesodermally-derived tissue, such as tissue derived from dorsal mesoderm; ectodermally-origin, such as tissue derived from the neural tube, neural crest, or head mesenchyme; or endodermally-derived tissue, such as tissue derived from the primitive gut.

Other biological activities of the subject ptc-2 proteins are described herein or will be reasonably apparent to those skilled in the art. According to the present invention, a polypeptide has biological activity if it is a specific agonist or antagonist of a naturally-occurring form of a ptc-2 protein.

Preferred nucleic acids encode a ptc-2 polypeptide comprising an amino acid sequence at least 80%, 85% or 90% homologous, more preferably at least 93% homologous and most preferably at least 95% homologous with an amino acid sequence of a naturally occurring ptc-2 protein, e.g., such as represented in SEQ ID No: 2. Nucleic acids which encode polypeptides at least about 98–99% homology with an amino acid sequence represented in SEQ ID No: 2 are of course also within the scope of the invention, as are nucleic acids identical in sequence with the enumerated ptc-2 sequence of the Sequence listing. In one embodiment, the nucleic acid is a cDNA encoding a polypeptide having at least one activity of the subject ptc-2 polypeptide.

Another aspect of the invention provides a nucleic acid which hybridizes under high or low stringency conditions to the nucleic acids represented by SEQ ID No: 1. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown in SEQ ID No: 1 due to degeneracy in the genetic code are also within the scope of the invention. Such nucleic acids encode functionally equivalent peptides (i.e., a peptide having a biological activity of a ptc-2 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a ptc-2 polypeptide. However, it is expected that DNA sequence polymorphisms that do lead to changes in the amino acid sequences of the subject ptc-2 polypeptides will exist among humans. One skilled in the art will appreciate that these variations in one or more nucleotides (up to about 3–5% of the nucleotides) of the nucleic acids encoding polypeptides having an activity of a ptc-2 polypeptide may exist among individuals of a given species due to natural allelic variation.

As used herein, a ptc-2 gene fragment refers to a nucleic acid having fewer nucleotides than the nucleotide sequence encoding the entire mature form of a ptc-2 protein yet which (preferably) encodes a polypeptide which retains some biological activity of the full length protein. Fragment sizes contemplated by the present invention include, for example, 5, 10, 25, 50, 75, 100, or 200 amino acids in length. In a preferred embodiment of a truncated receptor, the polypeptide will include all or a sufficient portion of the ligand domain to bind to a hedgehog polypeptide.

As indicated by the examples set out below, ptc-2 protein-encoding nucleic acids can be obtained from mRNA present in cells of metazoan organisms. It should also be possible to obtain nucleic acids encoding ptc-2 polypeptides of the present invention from genomic DNA from both adults and embryos. For example, a gene encoding a ptc-2 protein can be cloned from either a cDNA or a genomic library in accordance with protocols described herein, as well as those generally known to persons skilled in the art. A cDNA encoding a ptc-2 protein can be obtained by isolating total mRNA from a cell, such as a mammalian cell, e.g. a human cell, as desired. Double stranded cDNAs can be prepared from the total mRNA, and subsequently inserted into a suitable plasmid or bacteriophage vector using any one of a number of known techniques. The gene encoding a ptc-2 protein can also be cloned using established polymerase chain reaction techniques in accordance with the nucleotide sequence information provided by the invention. The nucleic acid of the invention can be DNA or RNA. A preferred nucleic acid is a cDNA including a nucleotide sequence represented by SEQ ID No: 1.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding a subject ptc-2 protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a ptc-2 protein. Alternatively, the antisense construct is an oligonucleotide probe which is generated ex vivo and which, when introduced into the cell causes inhibition of expression by hybridizing with the mRNA and/or genomic sequences of a ptc-2 gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidite, phosphorothioate and methylphosphonate analogs of DNA (see also U.S. Pat. Nos. 5,176,996; 5,264,564; and 5,256,775), or peptide nucleic acids (PNAs). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of a ptc-2 protein, e.g., by reducing the level of its expression, can be used in the manipulation of tissue, e.g. tissue maintenance, differentiation or growth, both in vivo and ex vivo.

Furthermore, the anti-sense techniques (e.g. microinjection of antisense molecules, or transfection with plasmids whose transcripts are anti-sense with regard to a ptc-2 mRNA or gene sequence) can be used to investigate the role of ptc-2 in developmental events, as well as the normal cellular function of ptc-2 in adult tissue. Such techniques can be utilized in cell culture, but can also be used in the creation of transgenic animals (described infra).

This invention also provides expression vectors containing a nucleic acid encoding a ptc-2 polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject ptc-2 proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding ptc-2 polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage X, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered. In one embodiment, the expression vector includes a recombinant gene encoding a polypeptide having an agonistic activity of a subject ptc-2 polypeptide, or alternatively, encoding a polypeptide which is an antagonistic form of the ptc-2 protein. An exemplary ptc-2 polypeptide of the present invention is a soluble truncated form of the protein which retains the ligand binding domain, e.g., retains the ability to bind to hedgehog polypeptides. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids, e.g., encoding either an agonistic or antagonistic form of a subject ptc-2 proteins or an antisense molecule described above. Thus, another aspect of the invention features expression vectors for in vivo or in vitro transfection and expression of a ptc-2 polypeptide or antisense molecule in particular cell types so as to reconstitute the function of, or alternatively, abrogate all or a portion of the biological function of ptc-2-induced transcription in a tissue in which the naturally-occurring form of the protein is misexpressed (or has been disrupted); or to deliver a form of the protein which alters maintenance or differentiation of tissue, or which inhibits neoplastic or hyperplastic proliferation.

Expression constructs of the subject ptc-2 polypeptides, as well as antisense constructs, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of ptc-2 expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA encoding the particular ptc-2 polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Retrovirus vectors, adenovirus vectors and adeno-associated virus vectors are exemplary recombinant gene delivery system for the transfer of exogenous genes in vivo, particularly into humans. These vectors provide efficient delivery of genes into cells, and the transferred nucleic acids are stably integrated into the chromosomal DNA of the host.

In addition to viral transfer methods, such as those illustrated above, non-viral methods can also be employed to cause expression of a subject ptc-2 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject ptc-2 polypeptide gene by the targeted cell. Exemplary gene delivery systems of this type include liposomal derived systems, poly-lysine conjugates, and artificial viral envelopes.

In clinical settings, the gene delivery systems for the therapeutic ptc-2 gene can be introduced into a patient-animal by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A ptc-2 gene can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the subject invention provides a "gene activation" construct which, by homologous recombination with a genomic DNA, alters the transcriptional regulatory sequences of an endogenous ptc-2 gene. For instance, the gene activation construct can replace the endogenous promoter of a ptc-2 gene with a heterologous promoter, e.g., one which causes constitutive expression of the ptc-2 gene or which causes inducible expression of the gene under conditions different from the normal expression pattern of ptc-2. A variety of different formats for the gene activation constructs are available. See, for example, the Transkaryotic Therapies, Inc. PCT publications WO93/09222, WO95/31560, WO96/29411, WO95/31560 and W094/12650.

In preferred embodiments, the nucleotide sequence used as the gene activation construct can be comprised of (1) DNA from some portion of the endogenous ptc-2 gene (exon sequence, intron sequence, promoter sequences, etc.) which direct recombination and (2) heterologous transcriptional regulatory sequence(s) which is to be operably linked to the coding sequence for the genomic ptc-2 gene upon recombination of the gene activation construct. For use in generating cultures of ptc-2 producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native ptc-2 gene. Such insertion occurs by homologous recombination, i.e., recombination regions of the activation construct that are homologous to the endogenous ptc-2 gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J. Exp. Med.*, 169:13), the human β-actin promoter (Gunning et al. (1987) *PNAS* 84:4831–4835), the glucocorticoid-inducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bernoist et al. (1981) *Nature* 290:304–310; Templeton et al. (1984) *Mol. Cell Biol.*, 4:817; and Sprague et al. (1983) *J. Virol.*, 45:773), the promoter contained in the 3' long terminal repeat of Rous sarcoma virus (RSV) (Yamamoto et al., 1980, *Cell*, 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics*, 1:379–384).

In still other embodiments, the replacement region merely deletes a negative transcriptional control element of the native gene, e.g., to activate expression, or ablates a positive control element, e.g., to inhibit expression of the targeted gene.

Another aspect of the present invention concerns recombinant forms of the ptc-2 proteins. Recombinant polypeptides preferred by the present invention, in addition to native ptc-2 proteins, are at least 85% or 90% homologous, more preferably at least 95% homologous and most preferably at least 98% homologous with an amino acid sequence represented by SEQ ID No: 2. Such polypeptides, as described above, include various truncated forms of the protein.

The term "recombinant ptc-2 polypeptide" refers to a polypeptide which is produced by recombinant DNA techniques, wherein generally, DNA encoding a ptc-2 polypeptide is inserted into a suitable expression vector which is in turn used to transform a host cell to produce the heterologous protein. Moreover, the phrase "derived from", with respect to a recombinant ptc-2 gene, is meant to include within the meaning of "recombinant protein" those proteins having an amino acid sequence of a native ptc-2 protein, or an amino acid sequence similar thereto which is generated by mutations including substitutions and deletions (including truncation) of a naturally occurring form of the protein.

The present invention further pertains to recombinant forms of the subject ptc-2 polypeptides which are encoded by genes derived from a mammal (e.g. a human), reptile or amphibian and which have amino acid sequences evolutionarily related to the ptc-2 protein represented in SEQ ID No: 2. Such recombinant ptc-2 polypeptides preferably are capable of functioning in one of either role of an agonist or antagonist of at least one biological activity of a wild-type ("authentic") ptc-2 protein of the appended sequence listing. The term "evolutionarily related to", with respect to amino acid sequences of ptc-2 proteins, refers to both polypeptides having amino acid sequences which have arisen naturally, and also to mutational variants of ptc-2 polypeptides which are derived, for example, by combinatorial mutagenesis.

The present invention also provides methods of producing the subject ptc-2 polypeptides. For example, a host cell transfected with a nucleic acid vector directing expression of a nucleotide sequence encoding the subject polypeptides can be cultured under appropriate conditions to allow expression of the peptide to occur. A cell culture includes host cells, media and other byproducts. Suitable media for cell culture are well known in the art. The recombinant ptc-2 polypeptide (e.g., soluble fragments) can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In other embodiments, the recombinant ptc-2 polypeptide is obtained from membrane preparations of the host cells.

This invention also pertains to a host cell transfected to express recombinant forms of the subject ptc-2 polypeptides. The host cell may be any eukaryotic or prokaryotic cell. Thus, a nucleotide sequence derived from the cloning of ptc-2 proteins, encoding all or a selected portion of a full-length protein, can be used to produce a recombinant form of a ptc-2 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. hedgehog proteins, TGFβ, proteins, as well as a wide range of receptors. Similar procedures, or modifications thereof, can be employed to prepare recombinant ptc-2 polypeptides by microbial means or tissue-culture technology in accord with the subject invention.

The recombinant ptc-2 genes can be produced by ligating nucleic acid encoding a ptc-2 polypeptide into a vector suitable for expression in either prokaryotic cells, eukaryotic cells, or both. Expression vectors for production of recombinant forms of the subject ptc-2 polypeptides include plasmids and other vectors. For instance, suitable vectors for the expression of a ptc-2 polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a ptc-2 polypeptide is produced recombinantly utilizing an expression vector generated by sub-cloning the coding sequence of a ptc-2 gene represented in SEQ ID No: 1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant ptc-2 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a ptc-2 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing ptc-2-derived polypeptides in a host which produces MAP (e.g., E. coli or CM89 or S. cerevisiae), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a ptc-2 protein. For example, the VP6 capsid protein of rotavirus can be used as an immunologic carrier protein for portions of the ptc-2 polypeptide, either in the monomeric form or in the form of a viral particle. The nucleic acid sequences corresponding to the portion of a subject ptc-2 protein to which antibodies are to be raised can be incorporated into a fusion gene construct which includes coding sequences for a late vaccinia virus structural protein to produce a set of recombinant viruses expressing fusion proteins comprising ptc-2 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a ptc-2 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a ptc-2 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of ptc-2 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the ptc-2 polypeptides of the present invention, particularly truncated forms of the ptc-2 protein. For example, ptc-2 polypeptides can be generated as glutathione-S-transferase (GST-fusion) proteins. Such GST-fusion proteins can enable easy purification of the ptc-2 polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The ptc-2 polypeptides may also be chemically modified to create ptc-2 derivatives by forming covalent or aggregate conjugates with other chemical moieties, such as glycosyl groups, lipids, cholesterol, phosphate, acetyl groups and the like. Covalent derivatives of ptc-2 proteins can be prepared by linking the chemical moieties to functional groups on amino acid sidechains of the protein or at the N-terminus or at the C-terminus of the polypeptide.

The present invention also makes available isolated ptc-2 polypeptides which are isolated from, or otherwise substantially free of other cellular proteins, especially receptors and/or other inductive polypeptides which may normally be associated with the ptc-2 polypeptide (such as smoothened). The term "substantially free of other cellular proteins" (also referred to herein as "contaminating proteins") or "substantially pure or purified preparations" are defined as encompassing preparations of ptc-2 polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified ptc-2 preparations will lack any contaminating proteins from the same animal from that ptc-2 is normally produced, as can be accomplished by recombinant expression of, for example, a mammalian ptc-2 protein in a yeast or bacterial cell.

As described above for recombinant polypeptides, isolated ptc-2 polypeptides can include all or a portion of an amino acid sequences corresponding to a ptc-2 polypeptide represented in SEQ ID No: 2 or homologous sequences thereto.

Isolated peptidyl portions of ptc-2 proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a ptc-2 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") ptc-2 protein. For example, Román et al. (1994) *Eur J Biochem* 222:65–73 describe the use of competitive-binding assays using short, overlapping synthetic peptides from larger proteins to identify binding domains.

The recombinant ptc-2 polypeptides of the present invention also include homologs of the authentic ptc-2 proteins, such as versions of those protein which are resistant to proteolytic cleavage, as for example, due to mutations which alter ubiquitination, prenylation or the like, enzymatic release of the extracellular domain, or other enzymatic targeting associated with the protein.

Modification of the structure of the subject ptc-2 polypeptides can be for such purposes as enhancing therapeutic or prophylactic efficacy, stability (e.g., ex vivo shelf life and resistance to proteolytic degradation in vivo), or post-translational modifications. Such modified peptides, when designed to retain at least one activity of the naturally-occurring form of the protein, or to produce specific antagonists thereof, are considered functional equivalents of the ptc-2 polypeptides (though they may be agonistic or antagonistic of the bioactivities of the authentic protein). Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur -containing= cysteine and methionine. (see, for example, Biochemistry, 2nd ed., Ed. by L. Stryer, W H Freeman and Co.: 1981). Whether a change in the amino acid sequence of a peptide results in a functional ptc-2 homolog (e.g. functional in the sense that the resulting polypeptide mimics or antagonizes the authentic form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial point mutants of the subject ptc-2 proteins as well as truncation mutants, and is especially useful for identifying potential variant sequences (e.g. homologs) that are functional in modulating signal transduction and/or ligand binding. The purpose of screening such combinatorial libraries is to generate, for example, novel ptc-2 homologs which can act as either agonists or antagonist, or alternatively, possess novel activities all together. To illustrate, ptc-2 homologs can be engineered by the present method to provide selective, constitutive activation of hedgehog activity, or alternatively, to be dominant negative inhibitors of ptc-2-dependent signal transduction. For instance, mutagenesis can provide ptc-2 homologs which are able to bind extracellular ligands yet be unable to bind or signal through intracellular regulatory proteins.

In one aspect of this method, the amino acid sequences for a population of ptc-2 homologs from different species or other related proteins are aligned, preferably to promote the highest homology possible. Such a population of variants can include, for example, ptc-2 homologs from one or more species. Amino acids which appear at each position of the aligned sequences are selected to create a degenerate set of combinatorial sequences. In a preferred embodiment, the variegated library of ptc-2 variants is generated by combinatorial mutagenesis at the nucleic acid level, and is encoded by a variegated gene library. For instance, a mixture of synthetic oligonucleotides can be enzymatically ligated into gene sequences such that the degenerate set of potential ptc-2 sequences are expressible as individual polypeptides, or alternatively, as a set of larger fusion proteins (e.g. for phage display) containing the set of ptc-2 sequences therein.

There are many ways by which such libraries of potential ptc-2 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential ptc-2 sequences. The synthesis of degenerate oligonucleotides is well known in the art (see for example, Narang, SA (1983) Tetrahedron 39:3; Itakura et al. (1981) Recombinant DNA, Proc 3rd Cleveland Sympos. Macromolecules, ed. A G Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a ptc-2 clone in order to generate a variegated population of ptc-2 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a ptc-2 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of ptc-2 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

In an exemplary embodiment, a library of extracellular fragments of ptc-2 variants are expressed as a fusion protein on the surface of a viral particle, and the viral particles panned on a hedgehog matrix. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461). For example, the recombinant phage antibody system (RPAS, Pharmacia Catalog number 2719400-01) can be easily modified for use in expressing and screening ptc-2 combinatorial libraries by panning on a matrix-immobilized hedgehog polypeptides to enrich for ptc-2 homologs with enhanced ability to bind the ligand.

In another embodiment, libraries of membrane-bound ptc-2 variants are expressed in a population of cells, which are subsequently used in a hedgehog binding assay.

The invention also provides for reduction of the ptc-2 protein to generate mimetics, e.g. peptide or non-peptide agents, which are able to disrupt a biological activity of a ptc-2 polypeptide of the present invention, e.g. as inhibitors of protein-protein interactions, such as with ligand proteins. Thus, such mutagenic techniques as described above are also useful to map the determinants of the ptc-2 proteins which participate in protein-protein interactions involved in, for example, interaction of the subject ptc-2 polypeptide with hedgehog polypeptides. Alternatively, a similar system can be used to derive fragments of a hedgehog protein which bind to a ptc-2 protein and competitively inhibit binding of the full length hedgehog protein.

To further illustrate, the critical residues of either a ptc-2 protein or a hedgehog protein which are involved in molecular recognition of the other can be determined and used to generate ptc-2-derived or hedgehog-derived peptidomimetics which competitively inhibit Hedgehog/ptc-2 protein interactions. By employing, for example, scanning mutagenesis to map the amino acid residues of a protein which is involved in binding other proteins, peptidomimetic compounds can be generated which mimic those residues which facilitate the interaction. Such mimetics may then be used to interfere with the normal function of a ptc-2 protein (or its ligand). For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc* Perkin Trans 1:1231), and b-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with a ptc-2 protein. For example, by using immunogens derived from a ptc-2 protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a ptc-2 polypeptide or an antigenic fragment which is capable of eliciting an antibody response). Techniques for conferring immunogenicity on a protein or peptide include conjugation to carriers or other techniques well known in the art. An immunogenic portion of a ptc-2 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a ptc-2 protein of a organism, such as a mammal, e.g. antigenic determinants of a protein represented by SEQ ID No: 2 or closely related homologs. In yet a further preferred embodiment of the present invention, in order to provide, for example, antibodies which are immuno-selective for discrete ptc-2 homologs the anti-ptc-2 polypeptide antibodies do not substantially cross react (i.e. does not react specifically) with a protein which is, for example, less than 85%, 90% or 95% homologous with the selected ptc-2. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target ptc-2.

Following immunization of an animal with an antigenic preparation of a ptc-2 polypeptide, anti-ptc-2 antisera can be obtained and, if desired, polyclonal anti-ptc-2 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a ptc-2 polypeptide of the present invention and monoclonal antibodies isolated from a culture comprising such hybridoma cells.

The term antibody as used herein is intended to include fragments thereof which are also specifically reactive with a ptc-2 polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a ptc-2 protein conferred by at least one CDR region of the antibody.

Both monoclonal and polyclonal antibodies (Ab) directed against authentic ptc-2 polypeptides, or ptc-2 variants, and antibody fragments such as Fab, F(ab)$_2$, Fv and scFv can be used to block the action of a ptc-2 protein and allow the study of the role of these proteins in, for example, differentiation of tissue. Experiments of this nature can aid in deciphering the role of ptc-2 proteins that may be involved in control of proliferation versus differentiation, e.g., in patterning and tissue formation.

Antibodies which specifically bind ptc-2 epitopes can also be used in immunohistochemical staining of tissue samples in order to evaluate the abundance and pattern of expression of each of the subject ptc-2 polypeptides. Anti-ptc-2 antibodies can be used diagnostically in immuno-precipitation and immuno-blotting to detect and evaluate ptc-2 protein levels in tissue as part of a clinical testing procedure. For instance, such measurements can be useful in predictive valuations of the onset or progression of proliferative or differentiative disorders. Likewise, the ability to monitor ptc-2 protein levels in an individual can allow determination of the efficacy of a given treatment regimen for an individual afflicted with such a disorder. The level of ptc-2 polypeptides may be measured from cells in bodily fluid, such as in samples of cerebral spinal fluid or amniotic fluid, or can be measured in tissue, such as produced by biopsy. Diagnostic assays using anti-ptc-2 antibodies can include, for example, immunoassays designed to aid in early diagnosis of a disorder, particularly ones which are manifest at birth. Diagnostic assays using anti-ptc-2 polypeptide antibodies can also include immunoassays designed to aid in early diagnosis and phenotyping neoplastic or hyperplastic disorders.

Another application of anti-ptc-2 antibodies of the present invention is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a ptc-2 protein, e.g. orthologs of the ptc-2 protein from other species, can then be detected with antibodies, as, for example, reacting nitrocellulose filters lifted from infected plates with anti-ptc-2 antibodies. Positive phage detected by this assay can then be isolated from the infected plate. Thus, the presence of ptc-2 homologs can be detected and cloned from other animals, as can alternate isoforms (including splicing variants) from humans.

Moreover, the nucleotide sequences determined from the cloning of ptc-2 genes from organisms will further allow for the generation of probes and primers designed for use in identifying and/or cloning ptc-2 homologs in other cell types, e.g. from other tissues, as well as ptc-2 homologs from other organisms. For instance, the present invention also provides a probe/primer comprising a substantially purified oligonucleotide, which oligonucleotide comprises a region of nucleotide sequence that hybridizes under stringent conditions to at least 15 consecutive nucleotides of sense or anti-sense sequence selected from the group consisting of SEQ ID No: 1 or naturally occurring mutants thereof. For instance, primers based on the nucleic acid represented in SEQ ID No: 1, can be used in PCR reactions to clone ptc-2 homologs. Likewise, probes based on the subject ptc-2 sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

Such probes can also be used as a part of a diagnostic test kit for identifying cells or tissue which misexpress a ptc-2 protein, such as by measuring a level of a ptc-2-encoding nucleic acid in a sample of cells from a patient-animal; e.g. detecting ptc-2 mRNA levels or determining whether a genomic ptc-2 gene has been mutated or deleted.

To illustrate, nucleotide probes can be generated from the subject ptc-2 genes which facilitate histological screening of intact tissue and tissue samples for the presence (or absence) of ptc-2-encoding transcripts. Similar to the diagnostic uses of anti-ptc-2 antibodies, the use of probes directed to ptc-2 messages, or to genomic ptc-2 sequences, can be used for both predictive and therapeutic evaluation of allelic mutations which might be manifest in, for example, degenerative disorders marked by loss of particular cell-types, apoptosis, neoplastic and/or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a ptc-2 protein. For instance, variation in polypeptide synthesis can be differentiated from a mutation in a coding sequence.

Accordingly, the present method provides a method for determining if a subject is at risk for a disorder characterized by aberrant apoptosis, cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a ptc-2-protein, or (ii) the mis-expression of the ptc-2 gene. To illustrate, such genetic lesions can be detected by ascertaining the existence of at least one of (i) a deletion of one or more nucleotides from a ptc-2 gene, (ii) an addition of one or more nucleotides to a ptc-2 gene, (iii) a substitution of one or more nucleotides of a ptc-2 gene, (iv) a gross chromosomal rearrangement of a ptc-2 gene, (v) a gross alteration in the level of a messenger RNA transcript of a ptc-2 gene, (vii) aberrant modification of a ptc-2 gene, such as of the methylation pattern of the genomic DNA, (vii) the presence of a non-wild type splicing pattern of a messenger RNA transcript of a ptc-2 gene, (viii) a non-wild type level of a ptc-2-protein, and (ix) inappropriate post-translational modification of a ptc-2-protein. As set out below, the present invention provides a large number of assay techniques for detecting lesions in a ptc-2 gene, and importantly, provides the ability to discern between different molecular causes underlying ptc-2-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a ptc-2 gene, such as represented by any one of SEQ ID No: 1, or naturally occurring mutants thereof, or 5' or 3' flanking sequences or intronic sequences naturally associated with the subject ptc-2 genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1944) PNAS 91:360–364), the later of which can be particularly useful for detecting point mutations in the ptc-2 gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a ptc-2 gene under conditions such that hybridization and amplification of the ptc-2 gene (if present) occurs, and (iv) detecting the presence or absence of an amplification product, or detecting the size of the amplification product and comparing the length to a control sample.

In still another embodiment, the level of a ptc-2-protein can be detected by immunoassay. For instance, the cells of a biopsy sample can be lysed, and the level of a ptc-2-protein present in the cell can be quantitated by standard immunoassay techniques. In yet another exemplary embodiment, aberrant methylation patterns of a ptc-2 gene can be detected by digesting genomic DNA from a patient sample with one or more restriction endonucleases that are sensitive to methylation and for which recognition sites exist in the ptc-2 gene (including in the flanking and intronic sequences). See, for example, Buiting et al. (1994) Human Mol Genet 3:893–895. Digested DNA is separated by gel electrophoresis, and hybridized with probes derived from, for example, genomic or CDNA sequences. The methylation status of the ptc-2 gene can be determined by comparison of the restriction pattern generated from the sample DNA with that for a standard of known methylation.

Furthermore, by making available purified and recombinant ptc-2 polypeptides, the present invention facilitates the development of assays which can be used to screen for drugs which are either agonists or antagonists of the normal cellular function of the subject ptc-2 proteins, or of their role in the pathogenesis of cellular maintenance, differentiation and/or proliferation and disorders related thereto. In a general sense, the assay evaluates the ability of a test compound to modulate binding between a ptc-2 polypeptide and a molecule, e.g., a ligand such as a hedgehog protein, that interacts with the ptc-2 polypeptide, or the ability of the test compound to induce intracellular signals in a ptc-2-dependent manner. Exemplary compounds which can be screened against such ptc-2-mediated interactions include peptides, nucleic acids, carbohydrates, small organic molecules, and natural product extract libraries, such as isolated from animals, plants, fungus and/or microbes.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with a ligand. Accordingly, in an exemplary screening assay of the present invention, a reaction mixture is generated to include at least a ligand-binding portion of a ptc-2 polypeptide, compound(s) of interest, and a "target molecule", e.g., a protein, which interacts with the ptc-2 polypeptide. Exemplary target molecules are the hedgehog proteins. Detection and quantification of interaction of the ptc-2 polypeptide with the target molecule provides a means for determining a compound's efficacy at inhibiting (or potentiating) interaction between the ptc-2 and the target molecule. The efficacy of the compound can be assessed by generating dose response curves from data obtained using various concentrations of the test compound. Moreover, a control assay can also be performed to provide a baseline for comparison. In the control assay, interaction of the ptc-2 polypeptide and target molecule is quantitated in the absence of the test compound.

Interaction between the ptc-2 polypeptide and the target molecule may be detected by a variety of techniques. Modulation of the formation of complexes can be quantitated using, for example, detectably labeled proteins such as radiolabelled, fluorescently labeled, or enzymatically labeled polypeptides, by immunoassay, by chromatographic detection, or by detecting the intrinsic activity of the acetylase.

Typically, it will be desirable to immobilize either ptc-2 or the target molecule to facilitate separation of complexes from uncomplexed forms of one or both of the proteins, as well as to accommodate automation of the assay. Binding of ptc-2 to the target molecule, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/ptc-2 (GST/ptc-2) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillanit), or in the supernatant after the complexes are subsequently dissociated. Alternatively, the complexes can be dissociated from the matrix, separated by SDS-PAGE, and the level of target molecule found in the bead fraction quantitated from the gel using standard electrophoretic techniques.

Other techniques for immobilizing proteins and other molecules on matrices are also available for use in the subject assay. For instance, either ptc-2 or target molecule can be immobilized utilizing conjugation of biotin and streptavidin. For instance, biotinylated ptc-2 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with ptc-2, but which do not interfere with the interaction between the ptc-2 and target molecule, can be derivatized to the wells of the plate, and ptc-2 trapped in the wells by antibody conjugation. As above, preparations of an target molecule and a test compound are incubated in the ptc-2-presenting wells of the plate, and the amount of complex trapped in the well can be quantitated. Exemplary methods for detecting such complexes, in addition to those described above for the GST-immobilized complexes, include immunodetection of complexes using antibodies reactive with the target molecule, or which are reactive with ptc-2 protein and compete with the target molecule; as well as enzyme-linked assays which rely on detecting an enzymatic activity associated with the target molecule, either intrinsic or extrinsic activity. In the instance of the latter, the enzyme can be chemically conjugated or provided as a fusion protein with the target molecule. To illustrate, the target molecule can be chemically cross-linked or genetically fused (if it is a polypeptide) with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating proteins trapped in the complex, antibodies against the protein, such as anti-ptc-2 antibodies, can be used. Alternatively, the protein to be detected in the complex can be "epitope tagged" in the form of a fusion protein which includes, in addition to the ptc-2 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

An exemplary drug screening assay of the present invention includes the steps of (a) forming a reaction mixture including: (i) a hedgehog polypeptide, (ii) a ptc-2 polypeptide, and (iii) a test compound; and (b) detecting interaction of the hedgehog and ptc-2 polypeptides. A statistically significant change (potentiation or inhibition) in the interaction of the hedgehog and ptc-2 polypeptides in the presence of the test compound, relative to the interaction in the absence of the test compound, indicates a potential agonist (mimetic or potentiator) or antagonist (inhibitor) of hedgehog bioactivity for the test compound. The reaction mixture can be a cell-free protein preparation, e.g., a reconstituted protein mixture or a cell lysate, or it can be a recombinant cell including a heterologous nucleic acid recombinantly expressing the ptc-2 polypeptide.

Where the desired portion of the hh receptor (or other hedgehog binding molecule) cannot be provided in soluble form, the cell-free system can be, e.g., a cell membrane preparation, a reconstituted protein mixture, or a liposome reconstituting the ptc-2 protein. For instance, the ptc-2 protein can be purified from detergent extracts from both authentic and recombinant origins can be reconstituted in artificial lipid vesicles (e.g. phosphatidylcholine liposomes) or in cell membrane-derived vesicles (see, for example, Bear et al. (1992) Cell 68:809–818; Newton et al. (1983) Biochemistry 22:6110–6117; and Reber et al. (1987) J Biol Chem 262:11369–11374). The lamellar structure and size of the resulting liposomes can be characterized using electron microscopy. External orientation of the ptc-2 protein in the reconstituted membranes can be demonstrated, for example, by immunoelectron microscopy. The interaction of a hedgehog protein with liposomes containing such ptc-2 complexes and liposomes without the protein, in the presence of candidate agents, can be compared in order to identify potential modulators of the hedgehog-ptc-2 polypeptide interaction. The reconstituted ptc-2 membrane systems can also include other proteins involved in hedgehog binding, e.g., such as smoothened.

In yet another embodiment, the drug screening assay is derived to include a whole cell expressing a ptc-2 polypeptide. The ability of a test agent to alter the activity of the ptc-2 protein can be detected by analysis of the recombinant cell. For example, agonists and antagonists of the ptc-2 biological activity can by detected by scoring for alterations in growth or differentiation (phenotype) of the cell. General techniques for detecting each are well known, and will vary with respect to the source of the particular reagent cell utilized in any given assay. For the cell-based assays, the recombinant cell is preferably a metazoan cell, e.g., a mammalian cell, e.g., an insect cell, e.g., a xenopus cell, e.g., an oocyte. In other embodiments, the hedgehog receptor can be reconstituted in a yeast cell.

In an exemplary embodiment, a cell which expresses the ptc-2 receptor, e.g., whether endogenous or heterologous, can be contacted with a ligand of the ptc-2 receptor, e.g., a hedgehog protein, which is capable of inducing signal transduction from the receptor, and the resulting signaling detected either at various points in the pathway, or on the basis of a phenotypic change to the reagent cell. In one embodiment, the reagent cell is contacted with antibody which causes cross-linking of the receptor, and the signal cascade induced by that cross-linking is subsequently detected. A test compound which modulates that pathway, e.g., potentiates or inhibits, can be detected by comparison with control experiments which either lack the receptor or lack the test compound. For example, visual inspection of the morphology of the reagent cell can be used to determine whether the biological activity of the targeted ptc-2 protein has been affected by the added agent.

In addition to morphological studies, change(s) in the level of an intracellular second messenger responsive to signaling by the ptc-2 polypeptide can be detected. For example, in various embodiments the assay may assess the ability of test agent to cause changes in phosphorylation patterns, adenylate cyclase activity (cAMP production), GTP hydrolysis, calcium mobilization, and/or phospholipid hydrolysis ($IP_3$, DAG production) upon receptor stimulation. By detecting changes in intracellular signals, such as alterations in second messengers or gene expression, in cells contacted with a hedgehog polypeptide, candidate agonists and antagonists to ptc-2-dependent hedgehog signaling can be identified.

The transduction of certain intracellular signals can be initiated by the specific interaction of an hh polypeptide with ptc-2 protein, while other signals can be indirectly altered by that interaction. In Drosophila, and presumptively in vertebrate cells as well, a number of gene products, including ptc-2, patched, the transcription factor cubitus interruptus (ci), the serine/threonine kinase fused (fu) and the gene products of costal-2, smoothened and suppressor of fused, have been implicated as putative components of hedgehog-dependent signal transduction pathways. The recent cloning of vertebrate homologs of the drosophila genes suggests that the hedgehog signaling pathway is highly conserved from drosophila to vertebrate species. The activity of each of these proteins can be detected directly (such as the kinase activity of fused, or can detected indirectly by monitoring the level of second messengers produced downstream in the signal pathway.

To further illustrate, recent studies have implicated protein kinase A (PKA) as a possible component of hedgehog signaling in drosophila and vertebrate organisms (Hammerschmidt et al. (1996) Genes & Dev 10:647). High PKA activity has been shown to antagonize hedgehog signaling in these systems. Although it is unclear whether PKA acts directly downstream or in parallel with hedgehog signaling, it is possible that hedgehog signaling occurring through a ptc-2 protein effects inhibition of PKA activity. Thus, detection of PKA activity provides a potential readout for the instant assays.

Binding of hedgehog to ptc-2 proteins may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) Environ Health Perspect 84:45–56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the drosophila gene fused (fu) which encodes a serine/threonine kinase has been identified as a potential downstream target in hedgehog signaling. (Preat et al., 1990 Nature 347, 87–89; Therond et al. 1993, Mech. Dev. 44. 65–80). The ability of compounds to modulate serine/threonine kinase activation could be screened using colony immunoblotting (Lyons and Nelson (1984) PNAS 81:7426–7430) using antibodies against phosphorylated serine or threonine residues. Reagents for performing such assays are commercially available, for example, phosphoserine and phosphothreonine specific antibodies which measure increases in phosphorylation of those residues can be purchased from commercial sources.

The interaction of a hedgehog protein with a ptc-2 protein may set in motion a cascade involving the activation and inhibition of downstream effectors, the ultimate consequence of which is, in some instances, a detectable change in the transcription or translation of a gene. Potential transcriptional targets of ptc-2-dependent hedgehog signaling include the ptc-2 gene itself, the patched gene (Hidalgo and Ingham (1990) *Development* 110, 291–301; Marigo et al. (1996) *Development* 122:1225–1233), and the vertebrate homologs of the drosophila cubitus interruptus (ci) gene, the GLI genes (Hui et al. (1994) *Dev Biol* 162:402–413). Patched gene expression has been shown to be induced in cells of the limb bud and the neural plate that are responsive to Shh. (Marigo et al. (1996) *PNAS*, in press; Marigo et al., supra). The GLI genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the GLI gene has been reported to be upregulated in response to hedgehog in limb buds, while transcription of the GLI3 gene is down-regulated in response to hedgehog induction (Marigo et al. (1996) *Development* 122:1225–1233). By selecting transcriptional regulatory sequences from such target genes, e.g. from Hip or GLI genes, that are responsible for the up- or down-regulation of these genes in response to hedgehog induction, and operatively linking such promoters to a reporter gene, the present invention provides a transcription based assay which is sensitive to the ability of a specific test compound to influence hedgehog signaling pathways.

In an exemplary embodiment, the step of detecting interaction of the hedgehog and ptc-2 polypeptides comprises detecting, in a cell-based assay, change(s) in the level of expression of a gene controlled by a transcriptional regulatory sequence responsive to signaling by the ptc-2 polypeptide. Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on hedgehog signaling. Expression of the reporter gene, thus, provides a valuable screening tool for the development of compounds that act as agonists or antagonists of ptc-2-dependent hedgehog induction.

In practicing one embodiment of the assay, a reporter gene construct is inserted into the reagent cell in order to generate a detection signal dependent on second messengers generated by ptc-2-dependent induction with a hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound or it may be compared with the amount of transcription in a substantially identical cell that lacks the target receptor protein. Any statistically or otherwise significant difference in the amount of transcription indicates that the test compound has in some manner altered the inductive activity of the hedgehog protein.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug. Many reporter genes are known to those of skill in the art and others may be identified or synthesized by methods known to those of skill in the art. A reporter gene includes any gene that expresses a detectable gene product, which may be RNA or protein.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Accordingly, yet another embodiment of the subject drug screening assays of the present invention provides a recombinant cell, e.g., for carrying out certain of the drug screening methods above, comprising: (i) an expressible recombinant gene encoding a heterologous ptc-2 polypeptide whose signal transduction activity is modulated by binding to a hedgehog protein; and (ii) a reporter gene construct containing a reporter gene in operative linkage with one or more transcriptional regulatory elements responsive to the signal transduction activity of the ptc-2 polypeptide. Still another aspect of the present invention provides a kit for screening test compounds to identify agents which modulate the binding of hedgehog proteins with a hedgehog receptor, including the above-referenced cell and a preparation of purified hedgehog polypeptide.

After identifying certain test compounds as potential modulators of one or more bioactivities of a ptc-2 protein (such as hedgehog binding), the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

Another aspect of the present invention relates to a method of inducing and/or maintaining a differentiated state, enhancing survival, and/or inhibiting (or alternatively potentiating) proliferation of a cell, by contacting the cells with an agent which modulates ptc-2-dependent signal transduction pathways. The subject method could be used to generate and/or maintain an array of different tissue both in vitro and in vivo. A "ptc-2 therapeutic," whether inhibitory or potentiating with respect to modulating the activity of a ptc-2 protein, can be, as appropriate, any of the preparations described above, including isolated ptc-2 polypeptides (including both agonist and antagonist forms), gene therapy constructs, antisense molecules, peptidomimetics, or agents identified in the drug assays provided herein. In certain embodiments, soluble forms of the ptc-2 protein including the extracellular ligand-binding domain of the receptor can be provided as a means for antagonizing the binding of a ptc-2 ligand to a cell-surface ptc-2 receptor. For instance, such forms of the receptor can be used to antagonize the bioactivity of a ligand of the receptor.

The ptc-2 therapeutic compounds of the present invention are likely to play an important role in the modulation of cellular proliferation and maintenance of, for example, neuronal, testicular, osteogenic or chondrogenic tissues during disease states. It will also be apparent that, by transient use of modulators of ptc-2 activities, in vivo reformation of tissue can be accomplished, e.g. in the development and maintenance of organs such as ectodermal patterning, as well as certain mesodermal and endodermal differentiation processes. By controlling the proliferative and differentiative potential for different cells, the subject ptc-2 therapeutics can be used to reform injured tissue, or to improve grafting and morphology of transplanted tissue. For instance, ptc-2 antagonists and agonists can be employed in a differential manner to regulate different stages of organ repair after physical, chemical or pathological insult. The present method is also applicable to cell culture techniques.

To further illustrate this aspect of the invention, in vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with aptc-2 therapeutic, e.g., such as an agent identified in the assays described above which potentiate ptc-2-dependent hedgehog bioactivities, in order to induce neuronal differentiation (e.g. of a stem cell), or to maintain the integrity of a culture of terminally-differentiated neuronal cells by preventing loss of differentiation. Alternatively, a antagonist of hedgehog induction, as certain of the ptc-2 homologs of the present invention are expected to be, can be used to prevent differentiation of progenitor cells in culture.

To further illustrate uses of ptc-2 therapeutics which may be either hedgehog agonists or antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The differential use of hedgehog agonists and antagonists in the culture can control the timing and type of differentiation accessible by the culture.

In addition to the implantation of cells cultured in the presence of hedgehog agonists and antagonists and other in vitro uses, yet another aspect of the present invention concerns the therapeutic application of a ptc-2 therapeutics to enhance survival of neurons and other neuronal cells in both the central nervous system and the peripheral nervous system. The ability of hedgehog protein to regulate neuronal differentiation during development of the nervous system and also presumably in the adult state indicates that certain of the hedgehog proteins, and accordingly ptc-2 therapeutic which modulate hedgehog bioactivities, can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject ptc-2 therapeutics to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/ inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a ptc-2 therapeutic that acts as a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of ptc-2 therapeutics in order to control, for example, differentiation and apoptotic events which give rise to loss of neurons (e.g. to enhance survival of existing neurons) as well as promote differentiation and repopulation by progenitor cells in the area affected.

In addition to degenerative-induced dementias, a pharmaceutical preparation of one or more of the subject ptc-2 therapeutics can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of a ptc-2 therapeutic can used to treat a restricted form of cerebellar cortical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a hedgehog agonist can be used alone, or in conjunction with other neurotrophic factors such as CNTF, BDNF or NGF to prevent and/or reverse motor neuron degeneration in ALS patients.

ptc-2 therapeutics of the present invention can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

Furthermore, a potential role for certain of the ptc-2 therapeutics derives from the role of hedgehog proteins in development and maintenance of dendritic processes of axonal neurons. Potential roles for hedgehog agonists consequently include guidance for axonal projections and the ability to promote differentiation and/or maintenance of the innervating cells to their axonal processes. Accordingly, compositions comprising ptc-2 therapeutics which agonize hedgehog activity, may be employed to support the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma infarction, infection (such as viral infection with varicella-zoster), metabolic disease, nutritional deficiency, toxic agents (such as cisplatin treatment).

Moreover, certain of the ptc-2 therapeutics (e.g., which antagonize hedgehog induction) may be useful in the selective ablation of sensory neurons, for example, in the treatment of chronic pain syndromes.

As appropriate, ptc-2 therapeutics can be used in nerve prostheses for the repair of central and peripheral nerve damage. In particular, where a crushed or severed axon is intubulated by use of a prosthetic device, certain of ptc-2 therapeutics can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide.

In another embodiment, the subject method can be used in the treatment of neoplastic or hyperplastic transformations such as may occur in the central nervous system. For instance, certain of the ptc-2 therapeutics which induce differentiation of neuronal cells can be utilized to cause such transformed cells to become either post-mitotic or apoptotic. Treatment with a ptc-2 therapeutic may facilitate disruption of autocrine loops, such as TGF-β or PDGF autostimulatory loops, which are believed to be involved in the neoplastic transformation of several neuronal tumors. ptc-2 therapeutics may, therefore, thus be of use in the treatment of, for example, malignant gliomas, medulloblastomas, neuroectodermal tumors, and ependymonas.

Yet another aspect of the present invention concerns the application of the discovery that hedgehog proteins are morphogenic signals involved in other vertebrate organogenic pathways in addition to neuronal differentiation as described above, having apparent roles in other endodermal patterning, as well as both mesodermal and endodermal differentiation processes. As described in the literature, Shh plays a role in proper limb growth and patterning by initiating expression of signaling molecules, including Bmp-2 in the mesoderm and Fgf-4 in the ectoderm. Thus, it is contemplated by the invention that compositions comprising certain of the ptc-2 therapeutics can also be utilized for both cell culture and therapeutic methods involving generation and maintenance of non-neuronal tissue.

In one embodiment, the present invention makes use of the discovery that hedgehog proteins, such as Shh, are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog agonists can be employed in the development and maintenance of an artificial liver which can have multiple metabolic functions of a normal liver. In an exemplary embodiment, a ptc-2 therapeutic which acts as a hedgehog agonist can be used to induce differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists can be utilized in conjunction with transplantation of such artificial livers, as well as embryonic liver structures, to promote intraperitoneal implantation, vascularization, and in vivo differentiation and maintenance of the engrafted liver tissue.

In yet another embodiment, ptc-2 therapeutics can be employed therapeutically to regulate such organs after physical, chemical or pathological insult. For instance, therapeutic compositions comprising hedgehog agonists can be utilized in liver repair subsequent to a partial hepatectomy. Similarly, therapeutic compositions containing hedgehog agonists can be used to promote regeneration of lung tissue in the treatment of emphysema.

In still another embodiment of the present invention, compositions comprising ptc-2 therapeutics can be used in the in vitro generation of skeletal tissue, such as from skeletogenic stem cells, as well as the in vivo treatment of skeletal tissue deficiencies. The present invention particularly contemplates the use of ptc-2 therapeutics which agonize a hedgehog a skeletogenic activity, such as an ability to induce chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignnent of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog agonist, particularly ptc-2 therapeutic which agonizes Ihh activity, to generate a cartilage repair response in the connective tissue by stimulating the differentiation and/or proliferation of chondrocytes embedded in the tissue. Induction of chondrocytes by treatment with a hedgehog agonist can subsequently result in the synthesis of new cartilage matrix by the treated cells. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrotic tissue by maintaining a constant production of new cartilage.

In an illustrative embodiment, the subject method can be used to treat cartilage of a diarthroidal joint, such as a knee, an ankle, an elbow, a ptc-2, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a ptc-2 therapeutic into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogenesis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a ptc-2 therapeutic during the culturing process, such as an Ihh agonist, in order to induce and/or maintain differentiated chondrocytes in the culture in order as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a ptc-2 therapeutic in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. Indian hedgehog is particularly associated with the hypertrophic chondrocytes that are ultimately replaced by osteoblasts. For instance, administration of a ptc-2 therapeutic of the present invention can be employed as part of a method for treating bone loss in a subject, e.g. to prevent and/or reverse osteoporosis and other osteopenic disorders, as well as to regulate bone growth and maturation. For example, preparations comprising hedgehog agonists can be employed, for example, to induce endochondral ossification, at least so far as to facilitate the formation of cartilaginous tissue precursors to form the "model" for ossification. Therapeutic compositions of ptc-2 therapeutics can be supplemented, if required, with other osteoinductive factors, such as bone growth factors (e.g. TGF-β factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds. However, it will be appreciated that hedgehog proteins, such as Ihh and Shh are likely to be upstream of BMPs, e.g. treatment with a hedgehog agonist will have the advantage of initiating endogenous expression of BMPs along with other factors.

In yet another embodiment, the ptc-2 therapeutic of the present invention can be used in the treatment of testicular cells, so as to modulate spermatogenesis. In light of the finding that hedgehog proteins are involved in the differentiation and/or proliferation and maintenance of testicular germ cells, hedgehog antagonist can be utilized to block the action of a naturally-occurring hedgehog protein. In a preferred embodiment, the ptc-2 therapeutic inhibits the biological activity of Dhh with respect to spermatogenesis, by competitively binding hedgehog in the testis. That is, the ptc-2 therapeutic can be administered as a contraceptive formulation. Alternatively, ptc-2 therapeutics which agonize the spermatogenic activity of Dhh can be used as fertility enhancers. In similar fashion, hedgehog agonists and antagonists are potentially useful for modulating normal ovarian function.

Another aspect of the invention features transgenic non-human animals which express a heterologous ptc-2 gene of the present invention, and/or which have had one or more genomic ptc-2 genes disrupted in at least a tissue or cell-types of the animal. Accordingly, the invention features an animal model for developmental diseases, which animal has one or more ptc-2 allele which is mis-expressed. For example, an animal can be generated which has one or more ptc-2 alleles deleted or otherwise rendered inactive. Such a model can then be used to study disorders arising from mis-expressed pte-2 genes, as well as for evaluating potential therapies for similar disorders.

The transgenic animals of the present invention all include within a plurality of their cells a transgene of the present invention, which transgene alters the phenotype of the "host cell" with respect to regulation by the ptc-2 protein, e.g., of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described herein and those generally known in the art.

In one embodiment, the transgene construct is a knockout construct. Such transgene constructs usually are insertion-type or replacement-type constructs (Hasty et al. (1991) *Mol Cell Biol* 11:4509). The transgene constructs for disruption of a ptc-2 gene are designed to facilitate homologous recombination with a portion of the genomic ptc-2 gene so as to prevent the functional expression of the endogenous ptc-2 gene. In preferred embodiments, the nucleotide sequence used as the knockout construct can be comprised of (1) DNA from some portion of the endogenous ptc-2 gene (exon sequence, intron sequence, promoter sequences, etc.) which direct recombination and (2) a marker sequence which is used to detect the presence of the knockout construct in the cell. The knockout construct is inserted into a cell, and integrates with the genomic DNA of the cell in such a position so as to prevent or interrupt transcription of the native ptc-2 gene. Such insertion can occur by homologous recombination, i.e., regions of the knockout construct that are homologous to the endogenous ptc-2 gene sequence hybridize to the genomic DNA and recombine with the genomic sequences so that the construct is incorporated into the corresponding position of the genomic DNA. The knockout construct can comprise (1) a full or partial sequence of one or more exons and/or introns of the ptc-2 gene to be disrupted, (2) sequences which flank the 5' and 3' ends of the coding sequence of the ptc-2 gene, or (3) a combination thereof.

A preferred knockout construct will delete, by targeted homologous recombination, essential structural elements of an endogenous ptc-2 gene. For example, the targeting construct can recombine with the genomic ptc-2 gene can delete a portion of the coding sequence, and/or essential transcriptional regulatory sequences of the gene.

Alternatively, the knockout construct can be used to interrupt essential structural and/or regulatory elements of an endogenous ptc-2 gene by targeted insertion of a polynucleotide sequence. For instance, a knockout construct can recombine with a ptc-2 gene and insert a nonhomologous sequence, such as a neo expression cassette, into a structural element (e.g., an exon) and/or regulatory element (e.g., enhancer, promoter, intron splice site, polyadenylation site, etc.) to yield a targeted ptc-2 allele having an insertional disruption. The inserted nucleic acid can range in size from 1 nucleotide (e.g., to produce a frameshift) to several kilobases or more, and is limited only by the efficiency of the targeting technique.

Depending of the location and characteristics of the disruption, the transgene construct can be used to generate a transgenic animal in which substantially all expression of the targeted ptc-2 gene is inhibited in at least a portion of the animal's cells. If only regulatory elements are targeted, some low-level expression of the targeted gene may occur (i.e., the targeted allele is "leaky").

The nucleotide sequence(s) comprising the knockout construct(s) can be obtained using methods well known in the art. Such methods include, for example, screening genomic libraries with ptc-2 cDNA probes in order to identify the corresponding genomic ptc-2 gene and regulatory sequences. Alternatively, where the cDNA sequence is to be used as part of the knockout construct, the cDNA may be obtained by screening a cDNA library as set out above.

In another embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method is to incubate the embryos in vitro for about 1–7 days, depending on the species, and then reimplant them into the surrogate host.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from excised tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

In one embodiment, gene targeting, which is a method of using homologous recombination to modify an animal's genome, can be used to introduce changes into cultured embryonic stem cells. By targeting the ptc-2 gene in ES cells, these changes can be introduced into the germlines of animals to generate chimeras. The gene targeting procedure is accomplished by introducing into tissue culture cells a DNA targeting construct that includes a segment homologous to a ptc-2 locus, and which also includes an intended sequence modification to the ptc-2 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a ptc-2 gene function through the use of a targeting transgene construct designed to undergo homologous recombination with ptc-2 genomic sequences. Targeting construct can be arranged so that, upon recombination with an element of a ptc-2 gene, a positive selection marker is inserted into (or replaces) coding sequences of the targeted ptc-2 gene. The inserted sequence functionally disrupts the ptc-2 gene, while also providing a positive selection trait.

Generally, the embryonic stem cells (ES cells) used to produce the knockout animals will be of the same species as the knockout animal to be generated. Thus for example, mouse embryonic stem cells will usually be used for generation of a ptc-2-knockout mice.

Embryonic stem cells are generated and maintained using methods well known to the skilled artisan such as those described by Doetschman et al. (1985) *J. EmbryoL Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation .

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct .

Screening can be accomplished using a variety of methods. Where the marker gene is an antibiotic resistance gene, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence. Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the ptc-2 coding sequence, transcriptional regulatory sequence, etc. Typically, less than about 1–5 percent of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent.

Offspring that are born to the foster mother may be screened initially for ptc-2 disruptants, DNA from tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from animals that are the product of this cross, as well as animals that are known heterozygotes and wild type animals.

Other means of identifying and characterizing the knock-out offspring are available. For example, Northern blots can be used to probe the mRNA for the presence or absence of transcripts of either the ptc-2 gene, the marker gene, or both. In addition, Western blots can be used to assess the (loss of) level of expression of the ptc-2 gene knocked out in various tissues of the offspring by probing the Western blot with an antibody against the ptc-2 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies or ptc-2 ligands, e.g., hedgehog proteins, to look for the presence or absence of the knockout construct gene product.

Animals containing more than one knockout construct and/or more than one transgene expression construct are prepared in any of several ways. The preferred manner of preparation is to generate a series of animals, each containing a desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s). Thus, a transgenic avian species can be generated by breeding a first transgenic bird in which the wild-type ptc-2 gene is disrupted with a second transgenic bird which has been engineered to express a mutant ptc-2 which retains most other biological functions of the receptor.

The transformed animals, their progeny, and cell lines of the present invention provide several important uses that will be readily apparent to one of ordinary skill in the art.

To illustrate, the transgenic animals and cell lines are particularly useful in screening compounds that have potential as prophylactic or therapeutic treatments of diseases such as may involve aberrant expression, or loss, of a ptc-2 gene, or aberrant or unwanted activation of receptor signaling. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

EXAMPLE 1

Cloning of Human ptc-2 cDNA for PCR was made from ClonTech human brain mRNA primed with random hexamers. Four PCR primers were made based on alignment analysis of ptc-1 amino acid sequences from different species (human, mouse, chick, zebrafish, and Drosophila) and the partial mouse ptc-2 sequence (T. Takabatake, et al., (1997) FEBS Letters 410:485): P106, CAAACTCCAAGGGGGCTCTG; P107, CACAAAGCCCAAGACCTGAG; P143, TGGAATTCT-TGGGTNGTNGC; P144, GAYTGYTTYTGGGARGG. Primers P143 and P144 were first used to enrich for ptc-2 DNA using the following PCR profile: 95° C. for 20 sec, 52° for 15 sec, and 72° C. for 30 sec. Then the PCR mixture was diluted 1:20 and used as template for nested PCR with P106 and P107 as primers. The correct-sized band was excised, cloned, and sequenced.

PCR primers were designed based on the resulting partial human ptc-2 sequence to perform RACE (Rapid Amplification of cDNA Ends) in both directions. The complete 5' coding region was identified with RACE, and about 700 bp of cDNA sequence was obtained on the 3' side. Two PCR primers were designed based on this 3' ) ptc-2 sequence, and used to screen a human amygdala cDNA library. A 2.5 kb clone was selected and sequenced.

All the 5' RACE sequence was either confirmed by an independent PCR fragment, or by a cDNA clone from a random-primed human fetal brain cDNA library (ClonTech).

The complete cDNA was assembled with the 2.5 kb cDNA clone, a 1.1 kb cDNA clone from the human fetal brain cDNA library, and a 1.7 kb PCR fragment which was sequenced completely.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

What is claimed is:

1. An isolated nucleic acid comprising a coding sequence for a human patched-2 (ptc-2) polypeptide at least 90% identical to SEQ ID No. 2, which ptc-2 polypeptide binds a naturally occurring hedgehog protein.

2. The nucleic acid of claim 1 wherein the polypeptide is at least 95% identical to SEQ ID No. 2.

3. The nucleic acid of claim 1 wherein the polypeptide is at least 98% identical to SEQ ID No. 2.

4. An expression vector comprising a nucleic acid of claim 1.

5. An isolated nucleic acid comprising a coding sequence for a polypeptide comprising a patched-2 (ptc-2) amino acid sequence that binds a naturally occurring hedgehog protein, which coding sequence hybridizes under stringent conditions including a wash step of 0.2×SSC at 50° C. to the sequence of SEQ ID. No. 1.

6. An expression vector comprising a nucleic acid of claim 5.

7. A nucleic acid comprising (i) a coding sequence for a polypeptide comprising a patched-2 (ptc-2) amino acid sequence that binds a naturally occurring hedgehog polypeptide, which coding sequence hybridizes under stringent conditions including a wash step of 0.2×SSC at 50° C. to the sequence of SEQ ID. No. 1; and (ii) a heterologous transcriptional regulatory sequence operably linked thereto.

8. An expression vector comprising a nucleic acid of claim 7.

9. A cell transfected with the nucleic acid of claim 5 or 7 and expressing said polypeptide.

10. An oligonucleotide probe comprising a nucleotide sequence which hybridizes under stringent conditions including a wash step of 0.2×SSC at 50° C. to a naturally occurring human patched-2 (ptc-2) gene having the sequence of SEQ ID No. 1, but not to a naturally occurring human patched-1 (ptc-1) gene.

11. A nucleic acid comprising (i) a coding sequence for a human patched-2 (ptc-2) polypeptide at least 95% identical to SEQ ID No. 2, which ptc-2 polypeptide binds a naturally occurring hedgehog protein and (ii) a heterologous transcriptional regulatory sequence operably linked thereto.

12. A cell comprising the nucleic acid of claim 11 and expressing the ptc-2 polypeptide.

13. An expression vector comprising a nucleic acid of claim 11.

* * * * *

UNITED STATES PATENT AND TRADEMARK OFFICE
CERTIFICATE OF CORRECTION

PATENT NO. : 6,309,879 B1
DATED : October 30, 2001
INVENTOR(S) : David A. Bumcrot It is certified that error appears in the above-identified patent and that said Letters Patent is hereby corrected as shown below:

<u>Title page,</u>
After "Inventor", please delete the middle initial: "H" and replace with the following text: -- A --

Signed and Sealed this

Twenty-sixth Day of March, 2002

Attest:

*Attesting Officer*

JAMES E. ROGAN
*Director of the United States Patent and Trademark Office*